United States Patent
Naor

(10) Patent No.: US 10,591,408 B2
(45) Date of Patent: Mar. 17, 2020

(54) FLOW CELL AND OPTICAL SYSTEM FOR ANALYZING FLUID

(71) Applicant: CI SYSTEMS (ISRAEL) LTD., Migdal Ha'emek (IL)

(72) Inventor: Yoram Naor, Givat Elah (IL)

(73) Assignee: CI SYSTEMS (ISRAEL) LTD., Migdal Ha'emek (IL)

( * ) Notice: Subject to any disclaimer, the term of this patent is extended or adjusted under 35 U.S.C. 154(b) by 40 days.

(21) Appl. No.: 16/001,966

(22) Filed: Jun. 7, 2018

(65) Prior Publication Data

US 2018/0364152 A1    Dec. 20, 2018

Related U.S. Application Data

(63) Continuation of application No. PCT/IL2018/050370, filed on Mar. 29, 2018.

(60) Provisional application No. 62/522,124, filed on Jun. 20, 2017.

(51) Int. Cl.
| | |
|---|---|
| *G01N 21/03* | (2006.01) |
| *G01N 21/01* | (2006.01) |
| *G01N 21/59* | (2006.01) |
| *G01N 21/05* | (2006.01) |

(52) U.S. Cl.
CPC ............ *G01N 21/01* (2013.01); *G01N 21/05* (2013.01); *G01N 21/59* (2013.01); *G01N 2021/0106* (2013.01); *G01N 2201/068* (2013.01); *G01N 2201/08* (2013.01); *G01N 2201/128* (2013.01)

(58) Field of Classification Search
CPC .................. G01N 21/01; G01N 21/59; G01N 2021/0106; G01N 2201/068; G01N 2021/015; G01N 21/0303; G02B 6/4214
See application file for complete search history.

(56) References Cited

U.S. PATENT DOCUMENTS

| | | | |
|---|---|---|---|
| 3,829,221 A | 8/1974 | Thomas et al. | |
| 5,218,428 A * | 6/1993 | Hoult | G01J 1/36 356/436 |
| 5,844,685 A | 12/1998 | Gontin | |
| 6,104,483 A | 8/2000 | Sebok et al. | |
| 7,515,259 B2 | 4/2009 | Hilmer et al. | |

(Continued)

FOREIGN PATENT DOCUMENTS

| | | |
|---|---|---|
| EP | 2977744 | 1/2016 |
| JP | 2004309296 | 11/2014 |

(Continued)

*Primary Examiner* — Hina F Ayub
*Assistant Examiner* — Rebecca C Bryant
(74) *Attorney, Agent, or Firm* — Mark M. Friedman

(57) ABSTRACT

A flow cell analyzes a fluid sample. A flow cell body contains a reference material and includes at least one hollow chamber to contain the fluid sample. Opposing surfaces of the flow cell body each have at least one transparent portion thereof. An optical path for light traversing through the flow cell body is defined in part by the transparent portions. A switching mechanism adjusts the amount of the reference material in the optical path to effect switching of the flow cell between a reference measurement state and a fluid sample measurement state. The reference measurement state corresponds to a first light intensity measurement and the fluid sample measurement state corresponds to a second light intensity measurement.

32 Claims, 16 Drawing Sheets

(56) References Cited

U.S. PATENT DOCUMENTS

| | | |
|---|---|---|
| 7,961,310 B1 | 6/2011 | Milosevic |
| 8,467,050 B2 | 6/2013 | Dutel |
| 2013/0215412 A1 | 8/2013 | Wynn |
| 2014/0300894 A1 | 10/2014 | Arimoto et al. |
| 2015/0276588 A1 | 10/2015 | Marshall et al. |
| 2016/0290915 A1 | 10/2016 | Chen et al. |
| 2016/0320288 A1 | 11/2016 | Fortin et al. |

FOREIGN PATENT DOCUMENTS

| | | |
|---|---|---|
| WO | 2016162541 | 10/2016 |
| WO | 2016170670 | 10/2017 |
| WO | 2016170681 | 10/2017 |

\* cited by examiner

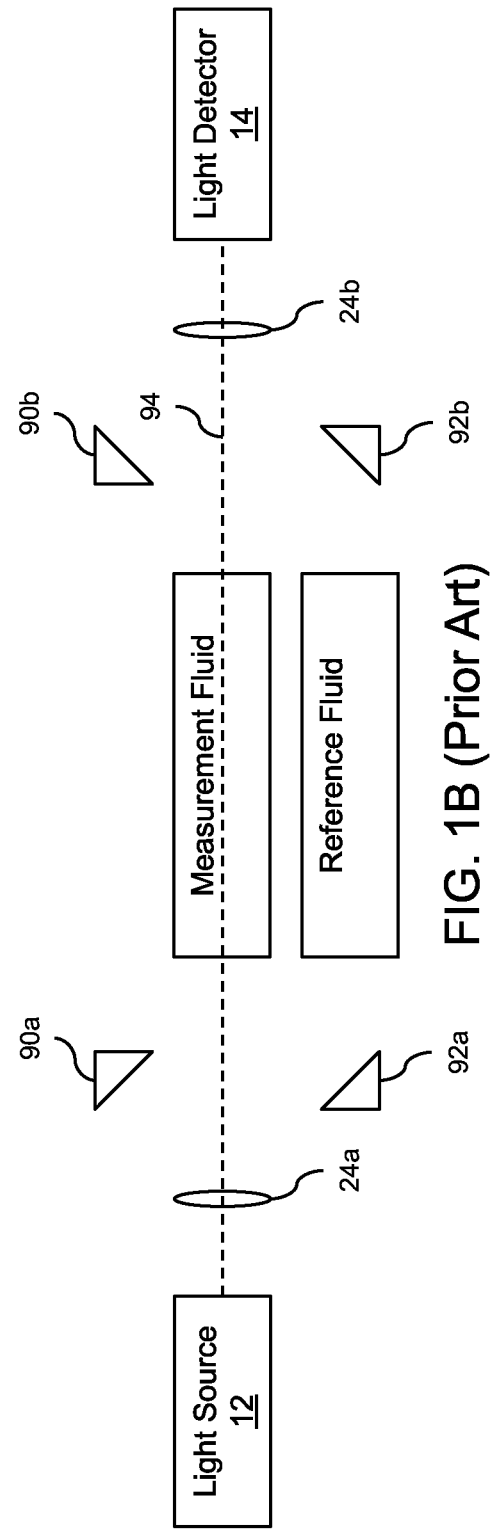

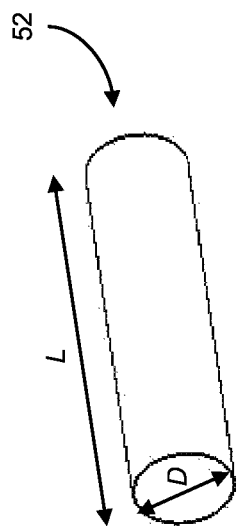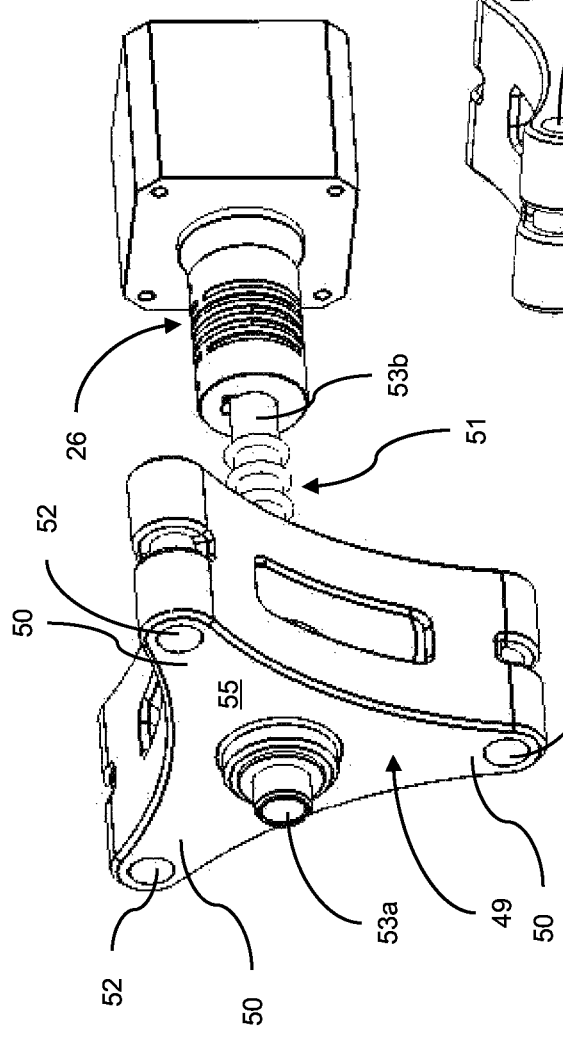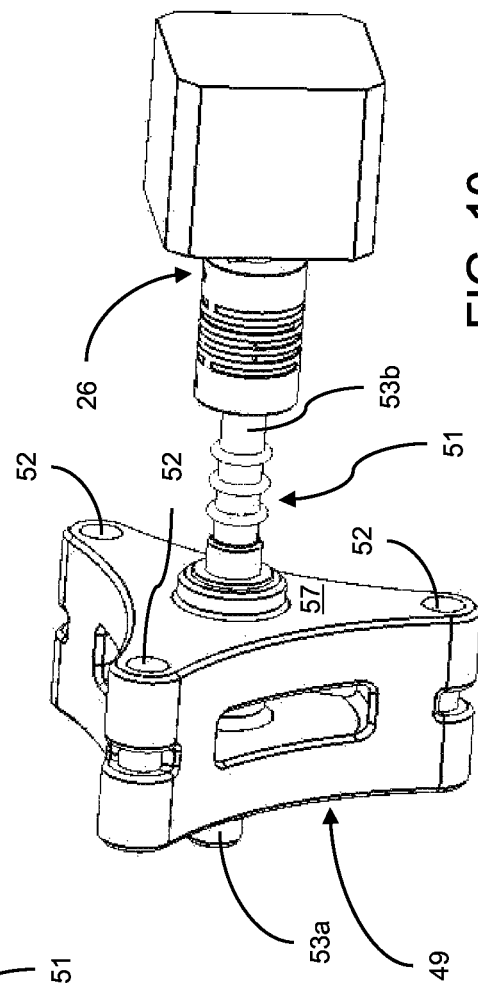

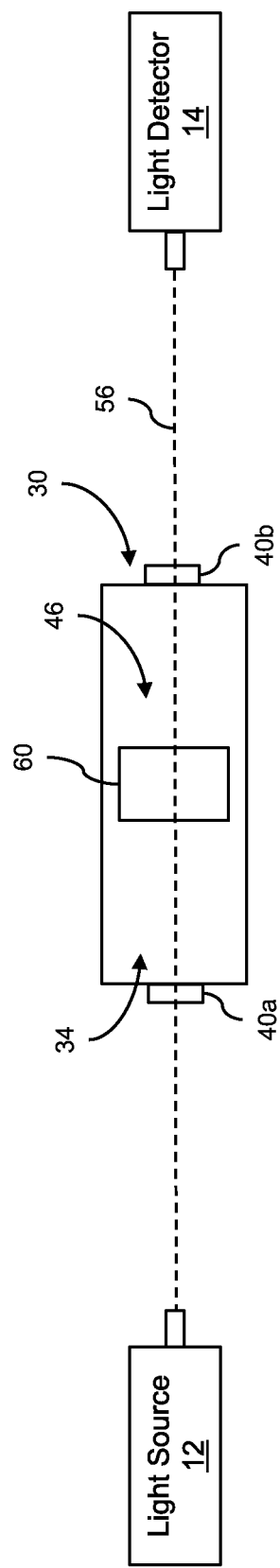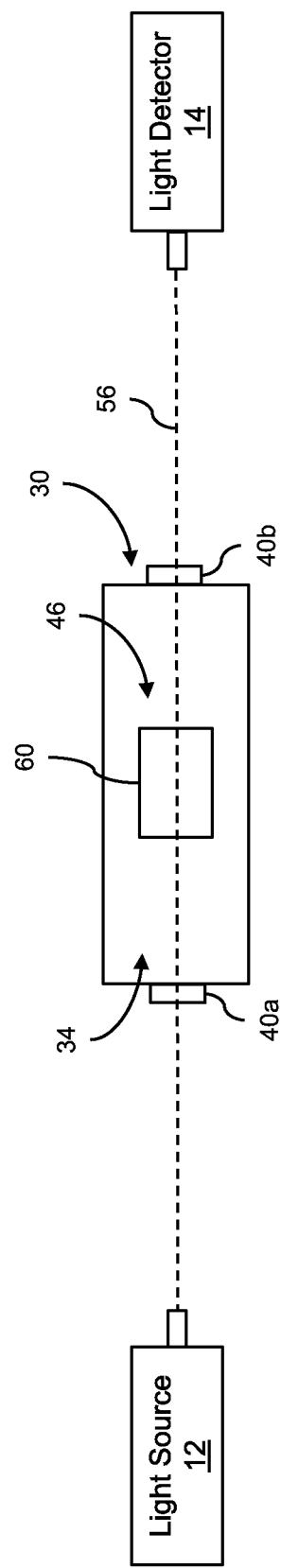
FIG. 13A
FIG. 13B

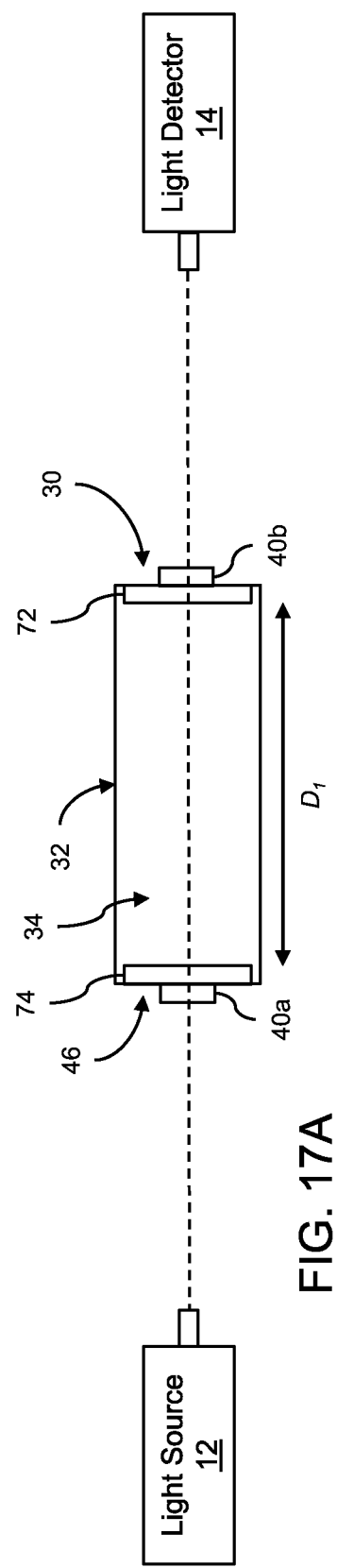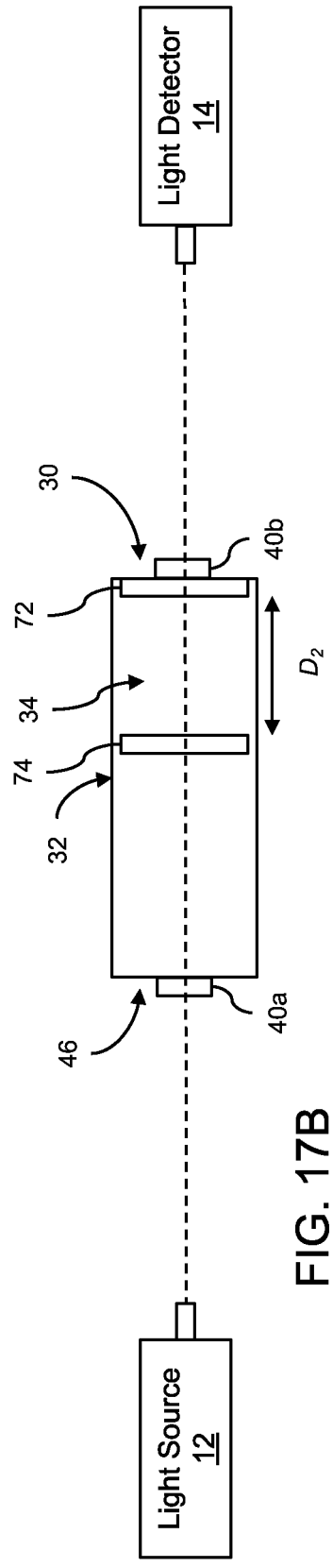
FIG. 17A
FIG. 17B

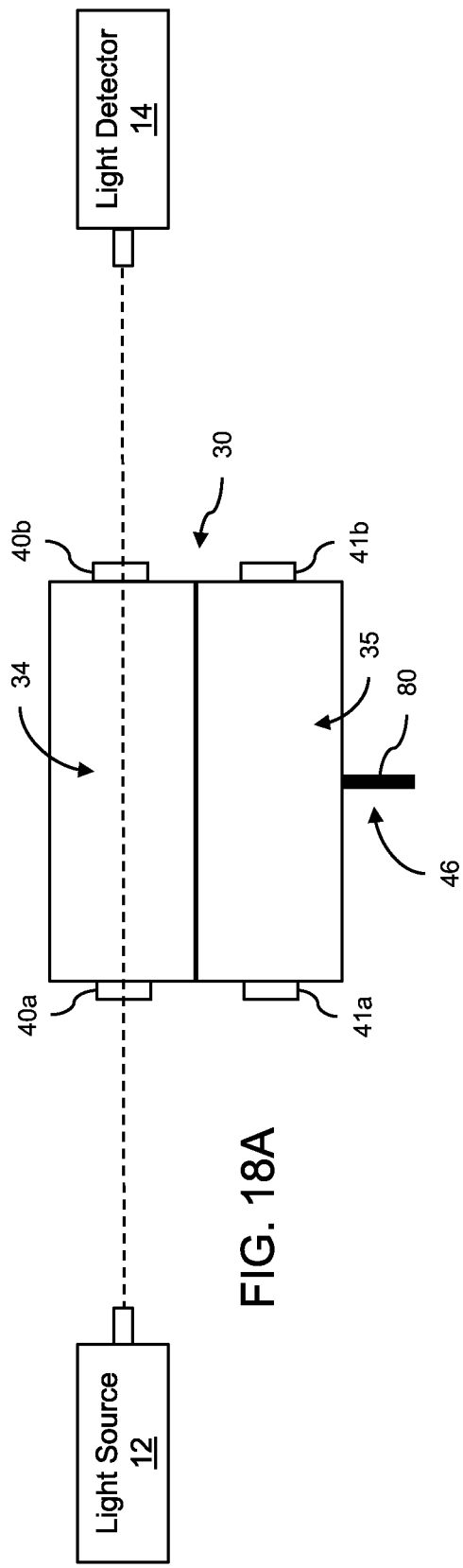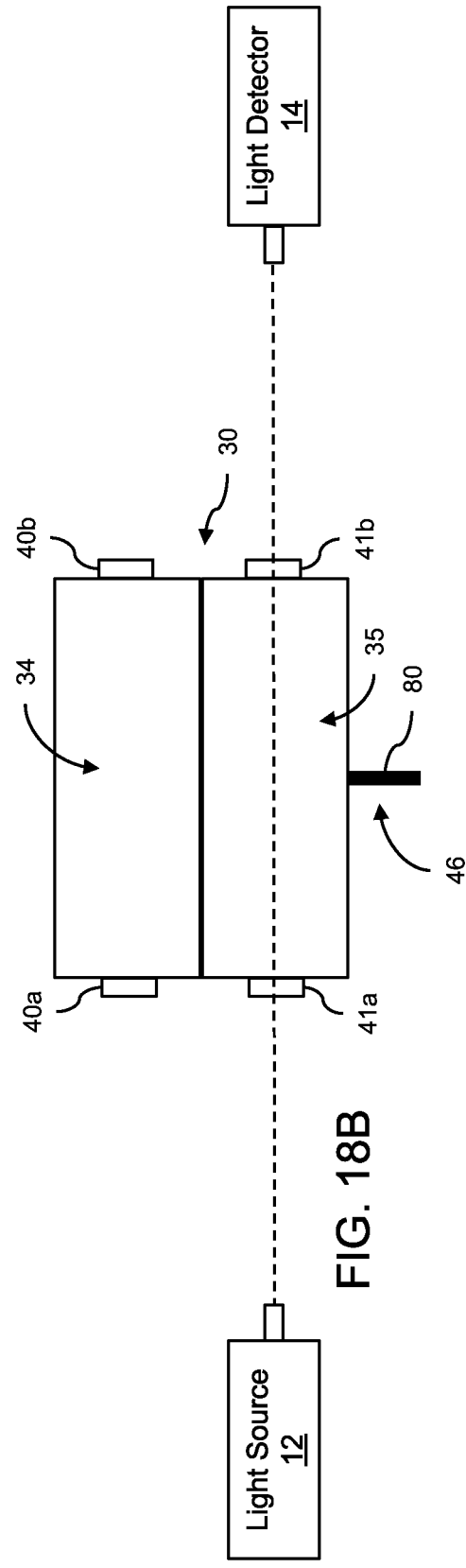

FLOW CELL AND OPTICAL SYSTEM FOR ANALYZING FLUID

CROSS-REFERENCE TO RELATED APPLICATIONS

This application claims priority from U.S. Provisional Patent Application No. 62/522,124, filed Jun. 20, 2017, whose disclosure is incorporated by reference in its entirety herein.

TECHNICAL FIELD

The present invention relates to flow cells and related systems for analyzing fluids.

BACKGROUND OF THE INVENTION

Solute concentration measurements generally use the well-known Beer-Lambert law, which relates the solute molecular density and molecular absorption cross-section coefficient with the light intensity transmitted through a certain path length of solution. In the case of uniform solute density, the relation can be expressed as follows:

$$I_1 = I_0 e^{-\alpha c l} \quad (1)$$

where $I_0$ is the light intensity entering the sampled solution, $I_1$ is the light intensity exiting the sampled solution, $\alpha$ is the molecular absorption cross-section coefficient, c is the molecular density of the solute molecules in the measured sample (also referred to as the "number density" or the "concentration"), and l is the length of the light path traversed by the light beam in the measured sample.

If $I_1$ is measured and $I_0$, $\alpha$, and l are known, the concentration c can be calculated using equation (1). For simplicity, the solvent is assumed to be transparent and any scattering effects of light caused by the solvent and/or solute molecules is assumed to be absent or negligible.

In laboratory instruments, the common practice used to measure an unknown concentration of a known solute in a fluid is to first measure the light transmittance, defined as the ratio $I_1/I_0$ from equation (1), through two measurement states using a light detector: a first measurement state, referred to as state A, in which the light is measured with no sample in the light path with the signal output of the light detector (referred to as the "reference measurement signal") being proportional to $I_0$; and a second measurement state, referred to as state B, in which the light is measured with the sample in the light path with the signal output of the light detector (referred to as the "sample measurement signal") being proportional to $I_1$. When using this methodology to measure the concentration, there is no need to accurately know the incoming light intensity $I_0$, as the incoming light intensity will cancel out in the light transmittance ratio ($I_1/I_0$).

When measuring flowing liquid samples in-line, it is usually cumbersome and impractical to introduce and remove the fluid sample from the light path as in states B and A above. A more widely used alternative methodology relies on an optical switching method, which makes the light beam travel first through the fluid sample and then through a second light path that does not include the fluid sample. This optical switching method is easier to implement, since the switching between the sample and no-sample measurement is done optically, by controlling optical elements external to the liquid stream. The path of state A, above, may be a path through air or vacuum, a path through the same solvent without solute, or a solution made of the same solvent and an accurately known concentration of the same solute material or any other material of known transmittance. In this way, the signal output of light detector in states A and B are obtained, and their ratio, corrected to the known transmittance of the reference sample, being equal to $I_1/I_0$, can be used to obtain the concentration c from equation (1) above, or using a similar equation, by using the knowledge of a and path length l.

FIGS. 1A and 1B illustrate a schematic representation of a typical scheme for implementing such an optical switching method. A light source 12 generates a beam of light which is directed by a first lens 24a and passes through either a reference fluid (FIG. 1A-state A) or the fluid sample (FIG. 1B-state B). The light beam that exits the reference or fluid sample is passed through a second lens 24b before impinging on a light detector 14. In state A (FIG. 1A), a pair of switching mirrors 90a and 90b are moved, such that the light beam from the light source 12, directed by the first lens 24a, is reflected from the first switching mirror 90a, off of a first fixed mirror 92a, to pass through the reference fluid, where the light beam is then reflected from a second fixed mirror 92b, and off of the second switching mirror 90b through the second lens 24b and to the light detector 14. In state B (FIG. 1B), the pair of switching mirrors 90a and 90b are moved such that the light beam from the light source 12, directed by the first lens 24a, passes through fluid sample, where the light beam then passes through the second lens 24b onto the light detector 14. The dashed line 94 represents the light path traversed by the light beam in the states A and B. Note that in the implementation illustrated in FIGS. 1A and 1B, the first lens 24a may be omitted if the light source 12 generates a directional beam of light.

One drawback of such an optical switching method and other conceptually similar methods is that the switching mechanism uses different external optical components in two different optical paths. In the scheme of FIGS. 1A and 1B, the mirrors 90a, 90b, 92a, and 92b are used to divert the light path from the sample when measuring the reference signal (FIG. 1A). As a result, the light exiting the two paths is in general affected not only by the presence or absence of the sample, but also by the reflectance and/or transmittance of the optical elements used in the optical trains. As a result, the ratio of the reference and sample measurement signals is not simply equal to the sample transmittance as desired: in fact, the ratio may also contain other factors such as, for example, i) the reflectivity ratios of the mirrors being used in states A and B, and ii) geometrical optical effects on the signal outputs in states A and B, due to the different shape of the two beams or the different distance that the beams travel in states A and B.

The sample measurement signal produced by the light detector 14 can be expressed as follows:

$$S_1 = I_{LS} R \tau_1 \tau_S \quad (2)$$

and the reference measurement signal produced by the light detector 14 can be expressed as follows:

$$S_0 = I_{LS} R \tau_0 \tau_R \quad (3)$$

where $I_{LS}$ is the light intensity output of the light source 12, $\tau_1$ is the optical throughput of the optical elements used in the sample measurement state (i.e., state A), $\tau_0$ is the optical throughput of the optical elements used in the reference measurement state (i.e., state B), $\tau_S$ is the optical throughput of the fluid sample, $\tau_R$ is the optical throughput of the reference material, and R is the response of the light detector 14. Defining the quantity $\rho_m$ as the ratio of the signals in equations (2) and (3) above, i.e., $S_1/S_0$, the ratio $\rho_m$ can be expressed as follows:

$$\rho_m = \tau_s \frac{\tau_1}{\tau_R \tau_0} \quad (4)$$

If the ratio $\tau_1/\tau_0$ is known and if the reference material transmission $\tau_R$ is known, the desired unknown quantity, $\tau_s$, which contains the concentration c information, can be obtained by inverting equation (4). In principle, the quantities $\tau_1$ and $\tau_0$ can be measured to achieve this end. However, besides the fact that such measurements are cumbersome and impractical, as well as expensive due to the requirement for additional optical switching components, any changes that occur over time to the optical elements used in one optical path but not the other (e.g., the switching mirrors used in state A but not in state B) will cause errors in the concentration measurement. An example of such a change may be a change in the reflectivity of one or more of the mirrors 90a, 90b, 92a, and 92b due to aging or accumulation of dust or other particles on the reflective mirror surfaces. Current practice cannot easily compensate for such temporal changes of optical components when implementing such optical switching mechanisms. Compensation for measurement system changes can only be done using specialized separate calibration procedures to characterize the measurement system itself. Such calibration procedures typically require a shutdown or temporary removal of the measurement system from the production line to perform the calibration, which degrades the efficiency of the concentration measurements. For simplicity, the treatment above does not take into account variations in f-number or differences in travelled distance, that may also be present, and therefore may also negatively affect the final result.

SUMMARY OF THE INVENTION

The present invention is directed to flow cells and optical analysis systems, that include a flow cell, for analyzing a fluid sample in a chamber of the flow cell, for example, a chemical solution of a solvent and solute, to determine the concentration of the solute. The analysis is performed by measuring the intensity of light that passes through the flow cell, and therefore through the fluid sample, in two measurement states. The flow cell and/or the optical analysis system include a switching mechanism that switches the flow cell between the two measurement states without moving any of the optical components of the optical analysis system external to the chamber of the flow cell, thereby reducing measurement errors. The switching between the two measurement states is affected by an adjustment of an amount of reference material, also contained within the flow cell, deployed in a light path through the flow cell.

In certain embodiments, the reference material is implemented as a chemically stable material, such as, for example, a transparent rod constructed from sapphire or quartz, allowing the operational properties of the optical analysis system and the flow cell to be maintained over long periods of time. In certain embodiments, by switching the flow cell between the two measurement states, the length of the light path traversed by light through the flow cell is switched between two optical path lengths (although the geometrical path length may remain the same). The components which induce the switching between the two path lengths are contained within the flow cell itself, thereby reducing the likelihood of the exposure of such components to external contamination.

According to the teachings of an embodiment of the present invention, there is provided a flow cell for analyzing a fluid sample. The flow cell comprises: a flow cell body containing a reference material and including at least one hollow chamber for containing the fluid sample, the flow cell body including opposing surfaces each having at least one transparent portion thereof, wherein an optical path for light to traverse through the flow cell body is defined in part by the transparent portions; and a switching mechanism operative to adjust an amount of the reference material deployed in the optical path to effect switching of the flow cell between a reference measurement state corresponding to a first light intensity measurement, and a fluid sample measurement state corresponding to a second light intensity measurement.

Optionally, the reference material includes at least one moveable element having at least one portion thereof in contact with the fluid sample.

Optionally, the switching mechanism includes a rotational mechanism having at least one rotating arm.

Optionally, the switching mechanism is operative to rotate the rotational mechanism to alternately position a transparent rod in and out of the optical path to effect switching between the two states.

Optionally, the rotational mechanism includes a plurality of arms, and wherein each arm has a transparent rod coupled thereto.

Optionally, the transparent rods of adjacent arms have different lengths.

Optionally, the reference material includes a transparent rod.

Optionally, the transparent rod is rotatable about a central axis of the flow cell body.

Optionally, the reference material further includes a second transparent rod, and wherein the two transparent rods are of different lengths.

Optionally, the two transparent rods are jointly moveable.

Optionally, the switching mechanism is operative to translationally move the transparent rod in and out of the optical path.

Optionally, the switching mechanism is operative to rotate the transparent rod about an axis of rotation that is substantially normal to the optical path.

Optionally, the reference material is moveable so as to displace an amount of the fluid sample in the optical path.

Optionally, the switching mechanism includes a piston arrangement.

Optionally, the hollow chamber includes an inlet port and an outlet port providing a flow path for the fluid to flow through the hollow chamber.

Optionally, the switching mechanism is actuated by the flow of the fluid through the hollow chamber.

Optionally, the switching mechanism is actuated by a motor operating in synchrony with a light detector.

Optionally, the reference measurement state corresponds to a first optical path length, and wherein the fluid sample measurement state corresponds to a second optical path length.

Optionally, the first optical path length corresponds to a first amount of the fluid sample in the optical path, and wherein the second optical path length corresponds to a second amount of the fluid sample in the optical path.

Optionally, the hollow chamber is fixedly positioned in the optical path.

Optionally, the transparent portions are implemented as a pair of transparent windows deployed on opposing surfaces of the hollow chamber.

Optionally, the reference material is deployed in the hollow chamber together with the fluid sample.

Optionally, the optical path is further defined in part by a static lens arrangement that includes a first lens and a second lens, and wherein the transparent portions are positionable between respective lenses of the static lens arrangement.

Optionally, the reference material is a second fluid different from the fluid sample.

Optionally, the flow cell body includes a second hollow chamber containing the second fluid.

Optionally, the transparent portions are implemented as a first pair of transparent windows deployed on opposing surfaces of the hollow chamber, and the flow cell further comprises: a second pair of transparent windows deployed on opposing surfaces of the second hollow chamber Optionally, when in the fluid sample measurement state, the pair of transparent windows are aligned with respective lenses of a static lens arrangement to provide a light path through the hollow chamber, and wherein when in the reference measurement state, the second pair of transparent windows are aligned with the respective lenses of the static lens arrangement to provide a light path through the second hollow chamber.

There is also provided according to an embodiment of the teachings of the present invention, a system for analyzing a fluid sample. The system comprises: a flow cell including a flow cell body that contains a reference material and includes at least one hollow chamber for containing the fluid sample; a static optical arrangement including at least a first and a second lens for directing light from a light source, through the flow cell body, to a light detector; at least a first and a second transparent surface deployed on opposing surfaces of the flow cell body, the flow cell body positionable to align the first transparent with the first lens and the second transparent surface with the second lens, wherein an optical path through the flow cell body is defined in part by the transparent surfaces and the static optical arrangement; and a switching mechanism operative to adjust an amount of the reference material deployed in the optical path to effect switching of the flow cell between a reference measurement state corresponding to a first light intensity measurement, and a fluid sample measurement state corresponding to a second light intensity measurement.

Optionally, the system further comprises: an optical fiber arrangement including a first optical fiber for guiding light into the flow cell to pass through the flow cell, and a second optical fiber for guiding the light that passed through the flow cell.

Optionally, the system further comprises: a light source coupled to the first optical fiber.

Optionally, the system further comprises: a light detector coupled to the second optical fiber for measuring an intensity of light passing through the flow cell body.

Optionally, the detector and the switching mechanism are configured to operate in synchrony.

Optionally, the system further comprises: a processing unit including at least one processor coupled to the detector, the processing unit configured to: receive a first signal indicative of the intensity of light passing through the flow cell body when the flow cell is in the reference measurement state, receive a second signal indicative of the intensity of light passing through the flow cell body when the flow cell is in the fluid sample measurement state, and determine at least one of a concentration or a transmission of the fluid sample based in part on the received signals.

There is also provided according to an embodiment of the teachings of the present invention, a flow cell for analyzing a fluid sample. The flow cell comprises: at least one hollow chamber for containing the fluid sample; a pair of transparent windows deployed on opposing surfaces of the hollow chamber, each of the transparent windows aligned with a respective lens of a static lens arrangement to define a light path through the hollow chamber; and a switching mechanism including at least one moveable element having at least one portion contacting the fluid sample, the switching mechanism operative to move the at least one element to change the length of the light path through the hollow chamber between at least a first light path length and a second light path length.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings:

FIGS. 1A and 1B are schematic representations of a prior art optical switching scheme used for measuring concentration of a solute;

FIGS. 9 and 10 are isometric views of the interconnection of the switching mechanism and the motor of the flow cell assembly of FIGS. 3 and 4, according to an embodiment of the invention;

FIG. 11 is an isometric view of a transparent rod of the switching mechanism of FIGS. 6, 7, 9 and 10, according to an embodiment of the invention;

FIGS. 13A and 13B are schematic representations of a flow cell having a switching mechanism implemented as a rotatable transparent rod, shown in a fluid sample measurement state and a reference measurement state, respectively, according to an embodiment of the invention;

FIGS. 17A and 17B are schematic representations of a flow cell having a switching mechanism implemented as a piston arrangement, shown in a fluid sample measurement state and a reference measurement state, respectively, according to an embodiment of the invention; and FIGS. 18A and 18B are schematic representations of a flow cell having a flow cell body subdivided into two jointly moveable chambers, with one chamber containing a fluid sample and the other chamber containing a reference fluid, shown in a fluid sample measurement state and a reference measurement state, respectively, according to an embodiment of the invention.

DESCRIPTION OF THE PREFERRED EMBODIMENTS

Figure 2:
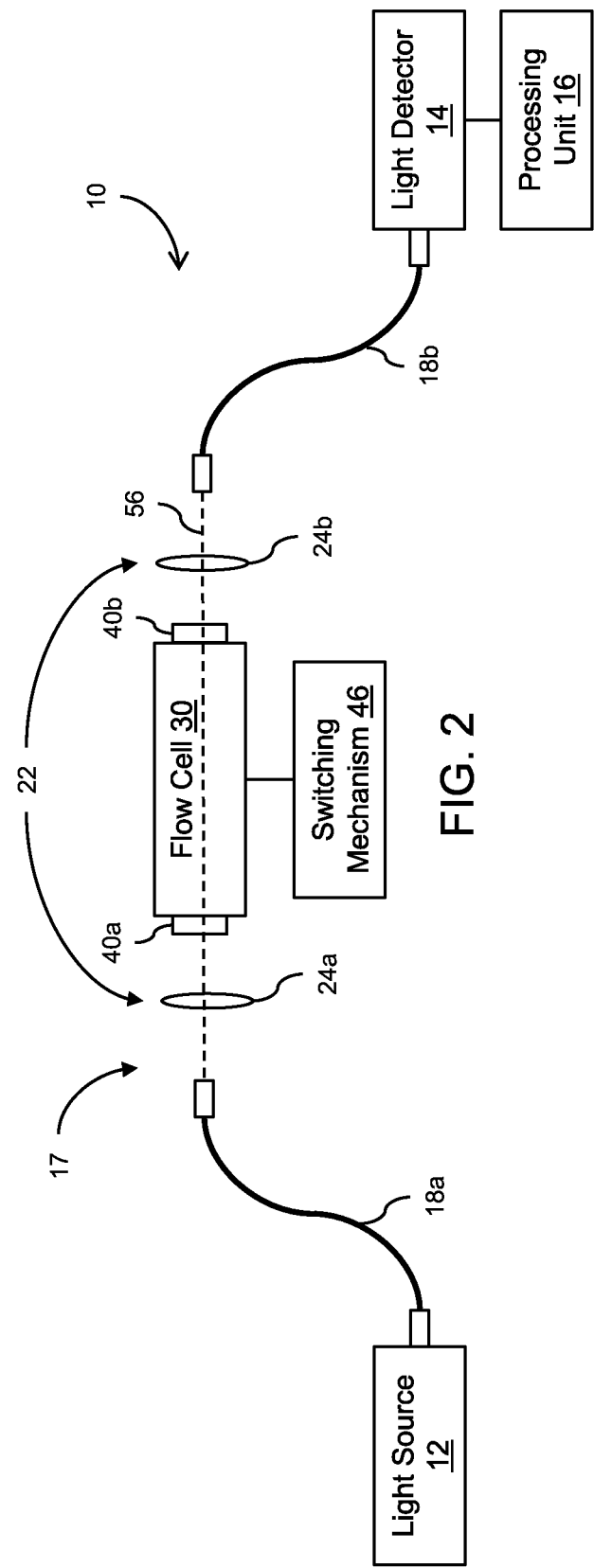
FIG. 2 is a schematic representation of a system that includes a flow cell for analyzing a fluid solution sample formed of a solvent and solute, to determine the concentration of the solute, according to an embodiment of the invention.

The present invention is directed to flow cells and optical analysis systems, that include a flow cell, for analyzing a fluid sample in a chamber of the flow cell, to determine physical properties of the fluid, such as concentration of components in the fluid, by measuring the fluid transmission.

The principles and operation of the flow cells and optical analysis systems according to present invention may be better understood with reference to the drawings accompanying the description.

The present invention is applicable to various types of fluids, including gases and various types of liquids, for example, chemical solutions made up of a solvent and solute, in which the flow cells and optical analysis systems are used to determine the concentration of the solute.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways. Initially, throughout this document, references are made to directions such as, for example, front and rear, clockwise and counter clockwise, and the like. These directional references are exemplary only to illustrate the invention and embodiments thereof.

Referring now to the drawings, FIG. 2 shows a schematic representation of a system, generally designated 10, constructed and implemented according to an embodiment of the present disclosure, for analyzing a fluid sample, for example, a chemical solution of a solvent and solute, to determine the concentration of the solute. Generally speaking, the system 10 includes a flow cell 30 for containing the fluid sample and at least one reference material, a light source 12, for example a halogen lamp, for irradiating the flow cell 30 with light, a light detector 14 for detecting the light that passes through the flow cell 30, and a light transmission assembly 17 for guiding the light from the light source 12 to the flow cell 30, and for guiding, to the light detector 14, the light that has passed through the flow cell 30. The schematic representation illustrated in FIG. 2 is one of various possible schematic representations of the system 10.

In certain embodiments, the flow cell 30 is directly built into a chemical delivery piping arrangement (not shown). For example, the flow cell 30 may be provided in a circulation path formed by such a piping arrangement connected to a chemical solution tank.

The light transmission assembly 17 includes a first optical fiber 18a, a second optical fiber 18b, and a static optical assembly 22 that includes a first static lens 24a and a second static lens 24b. Within the context of this document, the term "static" as referred to with respect to the components of the system 10 and the flow cell 30, generally refers to components which are fixed in position and do not move. Although represented in FIG. 2 as single lenses, each of the lenses 24a and 24b may actually be a set of more than one lens. The first optical fiber 18a is connected to the light source 12 and guides light from the light source 12, through the first lens 24a, into the flow cell 30. The first lens 24a acts to collimate the light from the light source 12 that passes into the flow cell 30. The second optical fiber 18b is connected to the light detector 14 and guides the light that has passed through the flow cell 30, and focused by the second lens 24b, to the light detector 14.

The lenses 24a and 24b of the optical assembly 22 can be aligned with respective transparent portions 40a and 40b of the flow cell 30, which provide entry and exit surfaces for the light to pass through the flow cell 30. The lenses 24a and 24b, together with the transparent portions of the flow cell 30, define an optical path 56 for the light from the light source 12 to pass through the flow cell 30 (i.e., a light path).

As will be discussed in further detail in subsequent sections of the present disclosure, the transparent portions 40a and 40b of the flow cell 30 may be implemented in the form of transparent windows which occupy sections or portions of oppositely disposed surfaces of the flow cell 30. Alternatively, the entirety or nearly the entirety of such oppositely disposed surfaces may be transparent. For simplicity, throughout the remainder of this document the transparent portions 40a and 40b are referred to interchangeably as transparent windows 40a and 40b. However, it should be clear that such windows are not strictly limited to minority sections or portions of the respective oppositely disposed surfaces of the flow cell 30 but may also include the entirety or nearly the entirety of the respective oppositely disposed surfaces of the flow cell 30.

The flow cell 30 includes a switching mechanism 46 for switching the flow cell 30, and the system 10, between a first measurement state and a second measurement state. Within the context of this document, the first measurement state is referred to interchangeably as a "fluid sample measurement state", a "sample measurement state", and the second measurement state is referred to interchangeably as a "reference measurement state" or a "calibration state". In certain embodiments, the switching between the two states is affected by the switching mechanism 46 adjusting the amount of the reference material that is deployed in the optical path 56, which by analogy adjusts the length of the optical path traversed by the light through the flow cell 30, and by further analogy adjusts the amount of the fluid sample, or the thickness of the fluid sample, that is in the optical path 56. In certain embodiments, the reference material is a transparent rod, which in certain implementations may be constructed from a chemically stable material, for example, sapphire or quartz. It is noted that construction of such transparent rods from sapphire may provide stability to the flow cell 30 in situations in which the fluid sample under analysis is an aggressive chemical solution. In other embodiments, the reference material may be the same solvent as the fluid sample without solute, a solution made of the same solvent and an accurately known concentration of the same solute material, or a fluid of known transmittance (e.g., air or deionized water).

In general, all of the components of the system 10 are static components, with the exception of the switching mechanism 46 and components which drive the switching mechanism 46. The collimated light beam that enters the flow cell 30 is neither diverged nor converged by the flow cell 30, meaning that the light beam is either parallel or normal to all of the optical surfaces of the system 10, which includes the lenses 24a and 24b, the portions 40a and 40b, and the various surfaces of the switching mechanism 46, as will be discussed in further detail in subsequent sections of the present disclosure. However, note that other implementations are possible in which the light entering the flow cell 30 is not necessarily collimated, and the light beam impinges the optical surfaces of the system 10 at oblique angles.

The system 10 further includes a processing unit 16 coupled to the light detector 14 for executing algorithms which calculate the transmittance and concentration of the fluid sample based on signals produced by the light detector 14 in the two measurement states. The processing unit 16 includes at least one processor coupled to a storage medium, such as a memory or the like. The processor can be any number of computer processors including, but not limited to, a microprocessor, an ASIC, a DSP, an FPGA, a state machine, and a microcontroller. Such processors include, or may be in communication with computer readable media, which stores program code or instruction sets that, when executed by the processor, cause the processor to perform actions. Types of computer readable media include, but are not limited to, electronic, optical, magnetic, or other storage or transmission devices capable of providing a processor with computer readable instructions. The algorithms and calculations executed by the processing unit 16 will be described in further detail in subsequent sections of the present disclosure.

Note that the optical assembly 22, the light source 12, and the light detector 14 may be embedded together with the flow cell 30 as part of a flow cell assembly, providing direct coupling of the light source 12 and the light detector 14 to the respective lenses 24a and 24b, thereby avoiding the need for optical fibers 18a and 18b.

Figure 3:
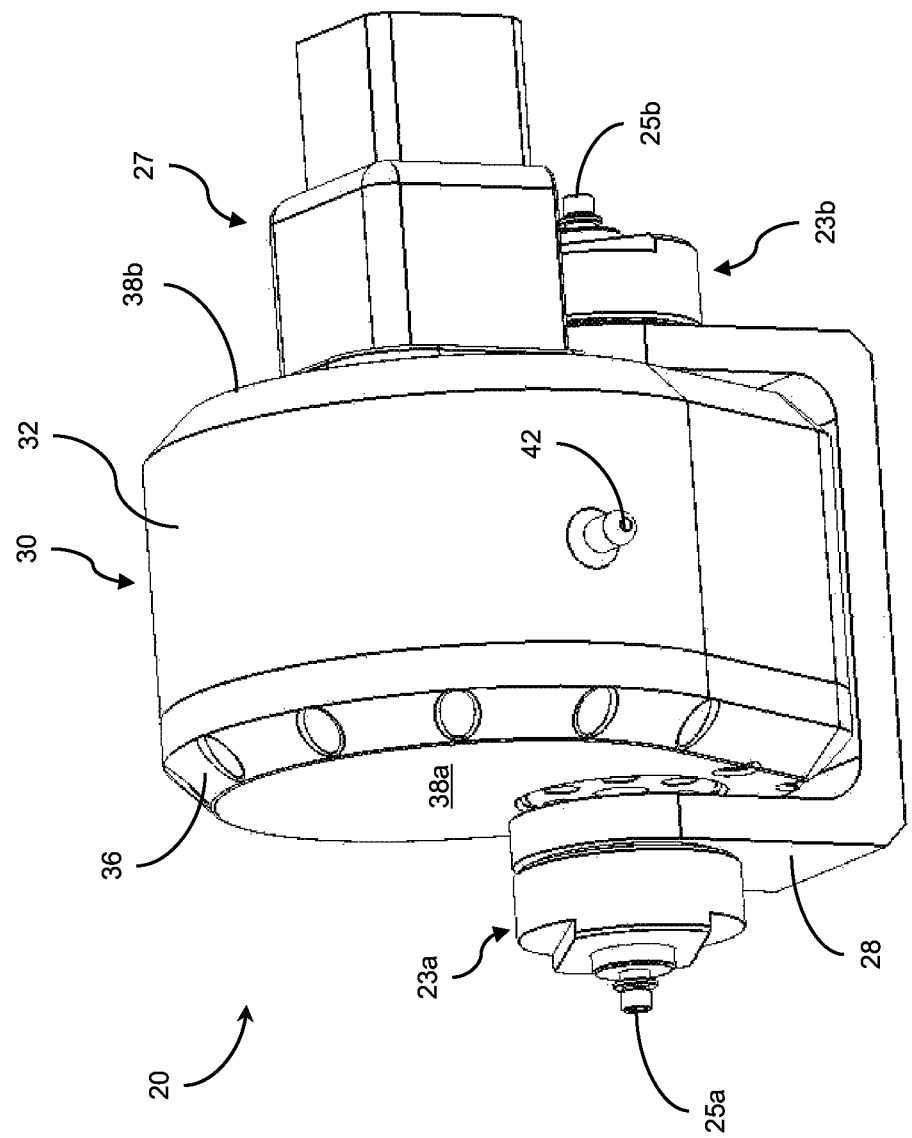
FIG. 3 is an isometric view of a flow cell assembly that includes a flow cell having a switching mechanism, implemented as a rotational switching mechanism, that switches between two measurement states for analyzing a fluid solution sample formed of a solvent and solute, to determine the concentration of the solute, according to an embodiment of the invention.
Figure 4:
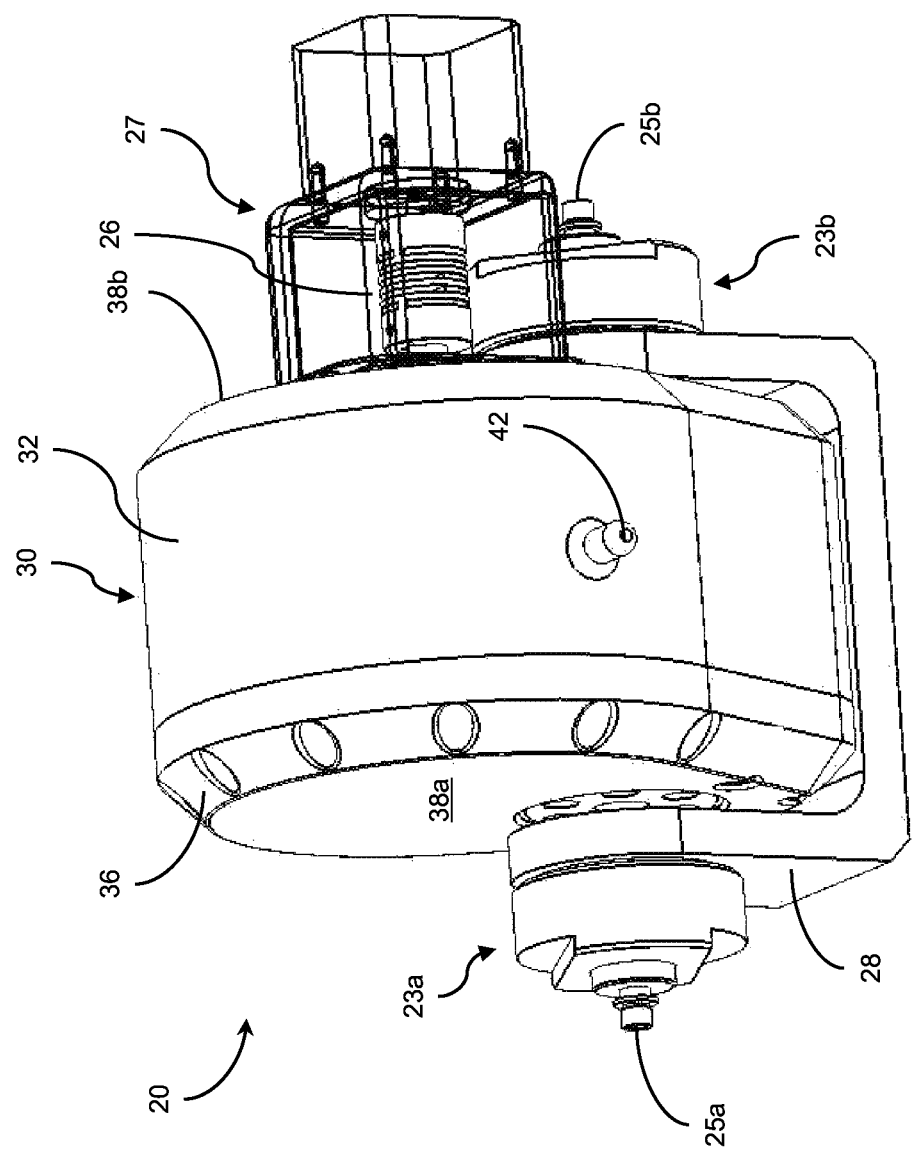
FIG. 4 is an isometric view similar to FIG. 3, showing a motor of the flow cell assembly, according to an embodiment of the invention.

With continued reference to FIG. 2, refer now to FIGS. 3-10, various views of an implementation of the flow cell 30, and corresponding components thereof, according to an embodiment of the present disclosure. As shown in FIGS. 3 and 4, the flow cell 30 is implemented as part of a flow cell assembly 20 that includes the optical assembly 22, a motor housing 27 that retains a motor 26 for actuating the switching mechanism 46, and a holder 28 for holding the flow cell 30, the optical assembly 22, and the motor housing 27 in place, allowing for the entire flow cell assembly 20 to be placed in-line with the light source 12 and the light detector 14. According to certain non-limiting implementations, the motor 26 is implemented as a stepper motor, providing the switching mechanism 46 with stepped switching capability.

The optical assembly 22 further includes an input arrangement 23a and an output arrangement 23b. The input arrangement 23a includes the lens 24a and a light input port 25a that receives light from the light source 12, via an input light-guiding element (e.g., optical fiber), and guides the light, through the lens 24a, to the flow cell 30. The output arrangement 23b includes the lens 24b and a light output port 25b, that receives the light, after passing through the flow cell 30 and the lens 24b, and guides the light, via an output light-guiding element (e.g., optical fiber) to the light detector 14. Note that the lens 24a may alternatively be separate from the input arrangement 23a, for example, the lens 24a may be deployed between the light source 12 and the input light-guiding element. Similarly, the lens 24b may be separate from the output arrangement 23b, for example, the lens may be deployed between the light detector 14 and the output light-guiding element.

The flow cell 30 includes a flow cell body 32 provided with oppositely disposed surfaces, namely a front surface 38a and a rear surface 38b. The flow cell 30 is deployed such that the front surface 38a is positioned proximate to the lens 24a, and the rear surface 38b is positioned proximate to the lens 24b. The front surface 38a is formed as part of a front cover 36 of the flow cell body 32.

Figure 5:
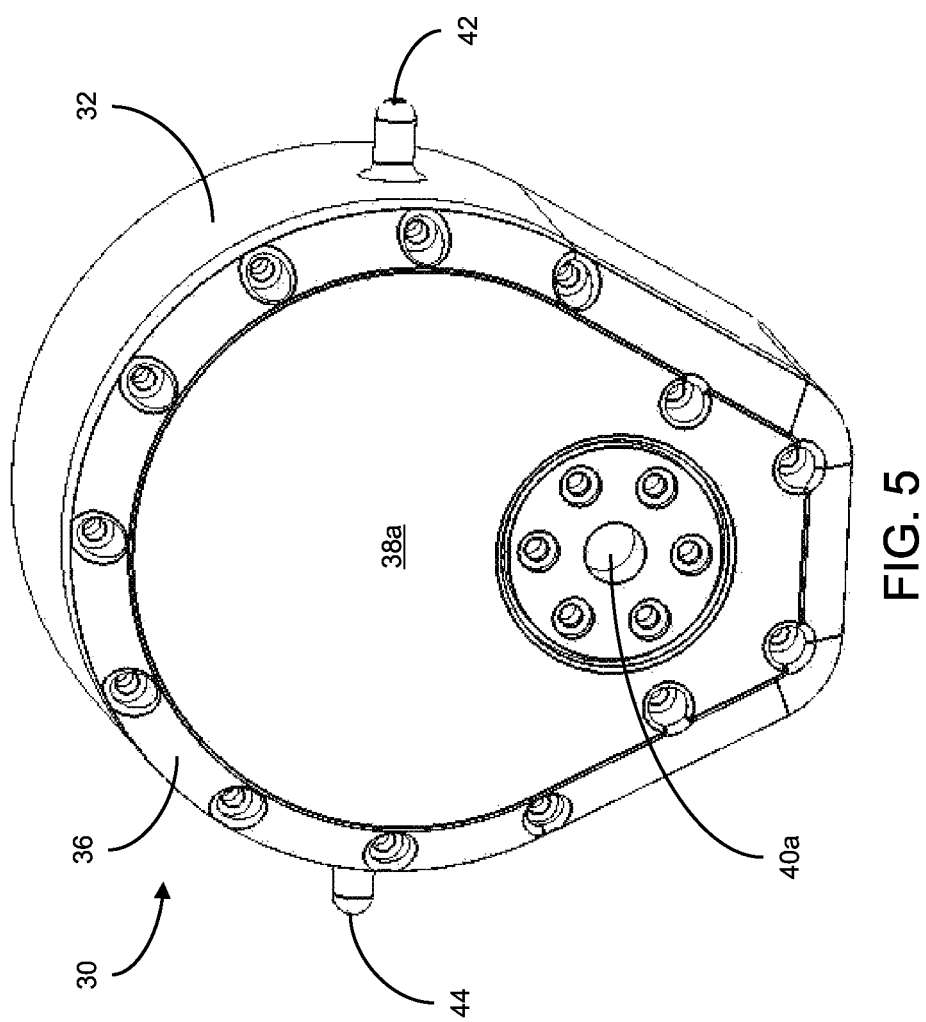
FIG. 5 is an isometric view of the flow cell of FIG. 3, taken from in front of the flow cell, according to an embodiment of the invention.
Figure 6:
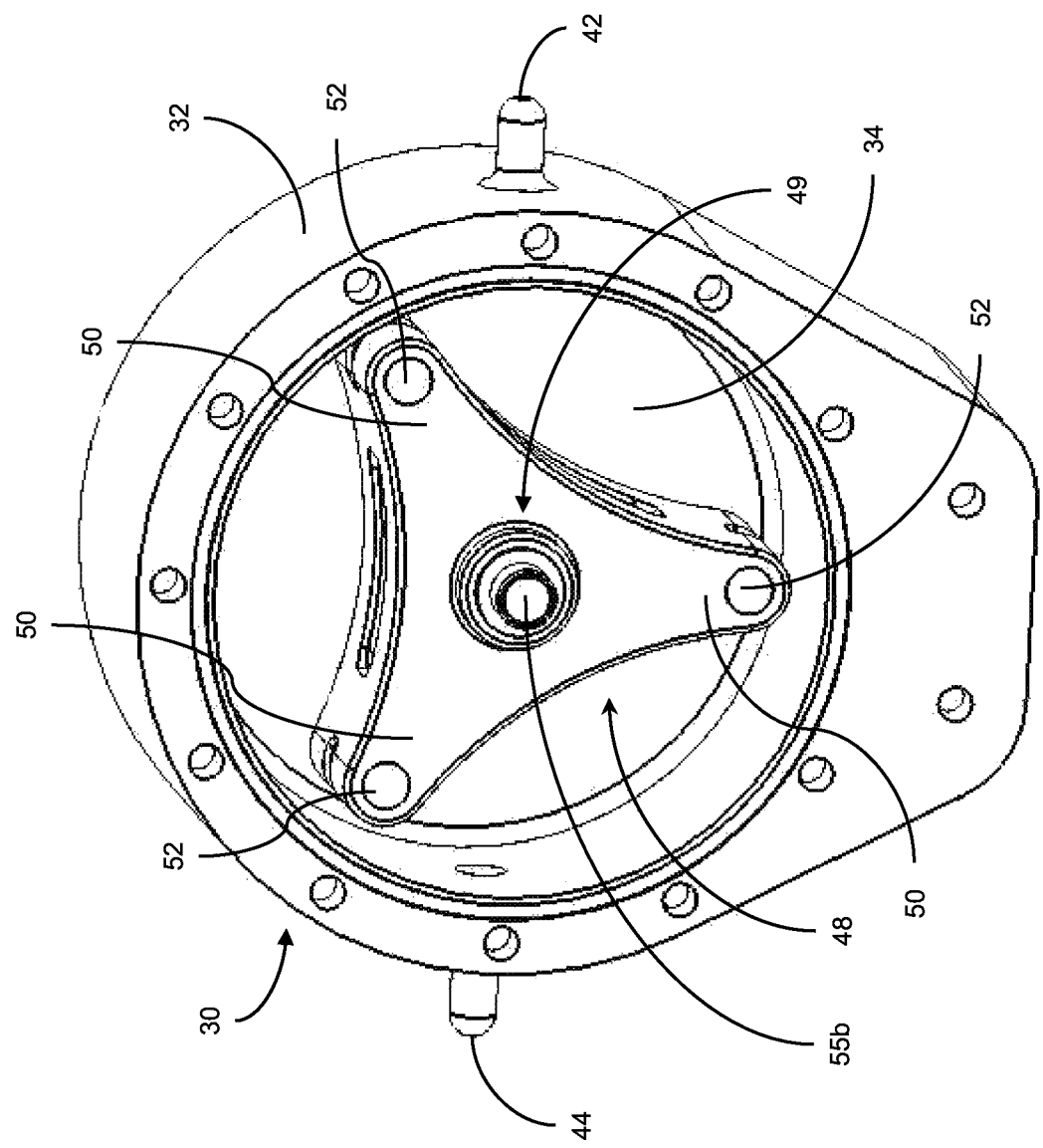
FIG. 6 is an isometric view similar to FIG. 5, with a front cover of the flow cell removed revealing components of the switching mechanism, according to an embodiment of the invention.
Figure 7:
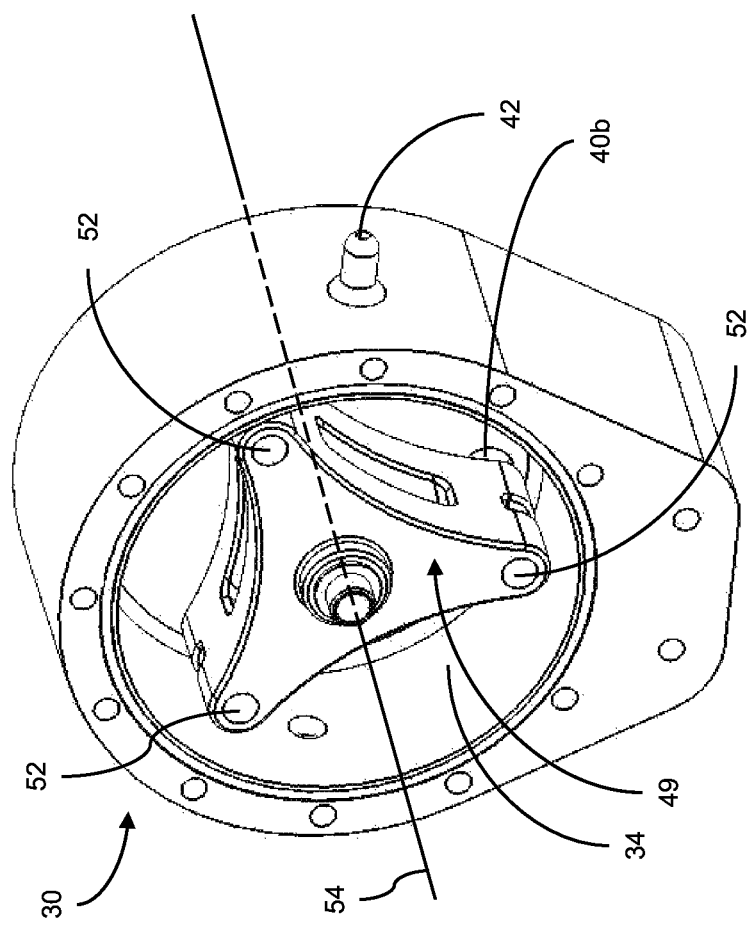
FIG. 7 is another isometric view of the flow cell similar to FIG. 6, according to an embodiment of the invention.
Figure 8:
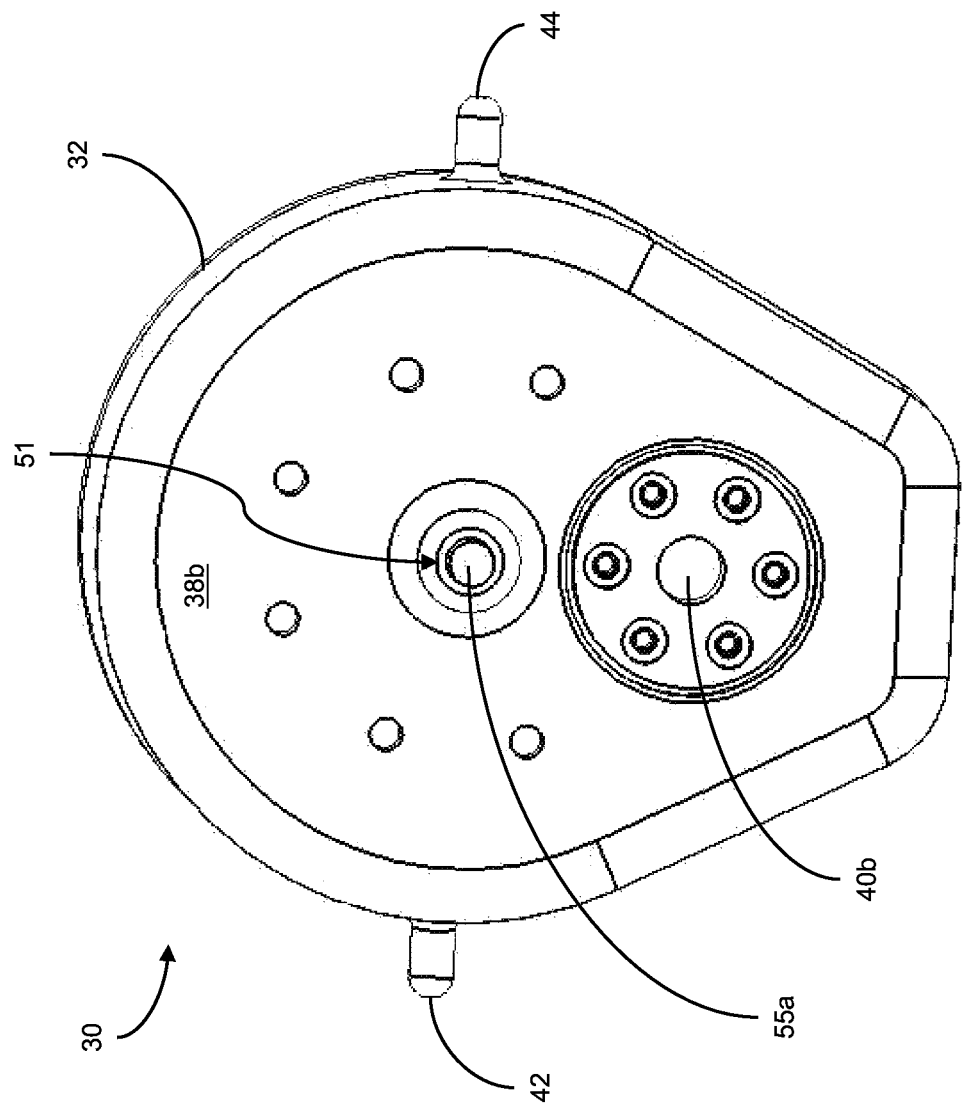
FIG. 8 is an isometric view of the flow cell of FIG. 3, taken from behind the flow cell, according to an embodiment of the invention.

To better demonstrate the components of the flow cell 30, FIGS. 5 and 8 illustrate isometric views of the flow cell 30 isolated from the flow cell assembly 20 taken from the front and back of the flow cell 30, respectively, and FIGS. 6 and 7 illustrate the flow cell 30 with the front cover 36 removed. A hollow chamber 34 is provided inside the flow cell body 32 to contain the fluid sample and the reference material. In certain embodiments, the hollow chamber 34 is fixedly positioned in the optical path 56.

With reference to FIGS. 5 and 8, the transparent windows 40a and 40b may be generally circular in shape and are deployed in respective surfaces 38a and 38b. Specifically, the transparent window 40a is deployed in the front surface 38a and is aligned with the lens 24a, and the transparent window 40b is deployed in the rear surface 38b and is aligned with the lens 24b. The transparent windows 40a and 40b are constructed from a material that is transparent in the spectrum of the light emitted by the light source 12.

The flow cell body 32 is further provided with an inlet port 42 and an outlet port 44 which provide a flow path for the fluid sample to flow through the hollow chamber 34 of the flow cell 30. The fluid sample is introduced into the flow cell 30 via the inlet port 42 and is expelled from the flow cell via the outlet port 44. In embodiments in which the flow cell 30 is provided in the circulation path formed by a chemical solution piping arrangement connected to a chemical solution tank, the ports 42 and 44 facilitate the flow of the fluid sample through the circulation path. In such embodiments, the inlet port 42 may receive the fluid sample from the chemical solution tank via an input portion of the chemical solution piping arrangement that is mutually connected to the chemical solution tank and the inlet port 42 at opposite ends thereof, and the outlet port 44 may provide the expelled fluid from the flow cell 30 to a sump tank (or recirculated back to the chemical solution tank) via an output portion of the chemical solution piping arrangement that is mutually connected to the sump tank (or chemical solution tank) and the outlet port 44 at opposite ends thereof.

The ports 42 and 44 may be respectively fitted with one-way valve arrangements to prevent back flow through the ports 42 and 44, ensuring unidirectional flow of the fluid sample through the flow cell 30.

In the implementation of the flow cell 30 illustrated in FIGS. 3-10, the switching mechanism 46 is deployed inside the hollow chamber 34 and is implemented as a rotational mechanism 48. With specific reference to FIGS. 6 and 7, the rotational mechanism 48 includes a rotatable base plate 49 with outwardly extending arm sections 50 that are in contact with the fluid sample. Each rotatable arm section 50 has a transparent rod 52, constructed from, for example, sapphire or quartz, attached thereto, which acts as the reference material.

As shown in FIGS. 9 and 10, the base plate 49 includes a front surface 55 and a rear surface 57. Each of the arm sections 50 may include an aperture (not shown) that extends from the front surface 55 to rear surface 57 of the base plate 49, to effectuate the attachment of the rods 52 to the respective arm sections 50. Each respective aperture and rod 52 pair is correspondingly sized and dimensioned, allowing the rods 52 to be slidably positioned or inserted into the respective apertures. The rods 52 may be held in place, in the respective apertures, via optical cement or the like.

The center of gravity of the front planar surface of the base plate 49 is aligned with a central axis 54 (as seen in FIG. 7) of the hollow chamber 34 of the flow cell body 32, allowing the base plate 49 to spin about the central axis 54 when actuated by the motor 26. As a result, the arm sections 50, and therefore the rods 52, of the rotational mechanism 48 rotate about the central axis 54 as the base plate 49 spins.

Refer now to FIGS. 9 and 10, interconnection of the motor 26 and the base plate 49. A drive shaft 51 having a first end region 53a and a second end region 53b connects the motor 26 to the base plate 49 and extends along the central axis 54 of the hollow chamber 34 of the flow cell body 32. The first end 53a extends out through a central portion (e.g., an aperture not shown) of the base plate 49, and the second end 53b extends out from the rear surface 38b of the flow cell body 32. The motor 26 actuates the rotational mechanism 48 to rotate by rotating the drive shaft 51, which causes the base plate 49 to spin, and thereby rotation (e.g., stepped rotation) of the arm sections 50 and rods 52 about the central axis 54. The induced rotation of the rods 52 thereby causes the end portions of the transparent rods 52 to intermittently align with the transparent windows 40a and 40b, resulting in the rods 52 being switchably positioned in and out of the optical path 56. According to certain embodiments, the light detector 14 and the motor 26, and therefore the rotational mechanism 48, are synchronized, such that the light detector 14 performs the light intensity measurements at the appropriate times. Note however that in certain embodiments, the synchronization between the light detector 14 and the motor 26 may not be necessary, for example in implementations in which synchronous signal acquisition and processing are not required.

Note that the rotation of the base plate 49 may be rotation in either a clockwise or counter clockwise direction and may be partial and/or non-continuous rotation. In a non-limiting example, in implementations in which the motor 26 is implemented as a stepper motor, the stepper motor can be controlled to allow stepped rotation in clockwise and counter clockwise directions. In another non-limiting example, the motor 26 may reach a limit switch to reverse the direction of rotation.

Although FIGS. 9 and 10 illustrate interfacing of the motor 26 to the base plate 49 via a mechanical linkage in the form of a drive shaft 51, it should be apparent to one of ordinary skill in the art that other mechanical linkages are possible, including linkages that include, for example, gears, cranks and/or any other mechanical linkage arrangements known in the art.

An example construction of the rod 52 is illustrated in FIG. 11, which depicts one of the rods 52 as a generally cylindrical structure having length L and circular base diameter D. The circular base portions of the rods 52 are of approximately the same size as the transparent windows 40a and 40b. The rods 52 are oriented such that the length L of each of the rods 52 extends from the front surface 38a toward the rear surface 38b of the flow cell body 32. Rotation of the rotational mechanism 48 causes the circular base portions of the rods 52 to intermittently align with the transparent windows 40a and 40b. The alignment of the one of the rods 52 with the transparent window 40b is shown in FIG. 7, for clarity of illustration.

Note that although the drawings show a rotational mechanism 48 having three rotatable arm sections 50, with the rods 52 attached to the arm sections 50 being of equal length, other implementations are possible, in which the rotational mechanism 48 includes one rotatable arm section having a single rod attached thereto. Alternatively, the rotational mechanism 48 may include two rotatable arm sections, with the rods attached to the arm sections being of different lengths in the dimension of the central axis 54. For example, one of the arm sections may have a 15-millimeter (mm) rod attached thereto, and the other arm section may have a 5 mm rod attached thereto. Moreover, the rotational mechanism 48 may include more than three rotatable arms, for example, six arms, with neighboring arms having rods of identical or different lengths. For example, a first arm section may have a 15 mm rod attached thereto, a second arm section neighboring the first arm section may have a 5 mm rod attached thereto, a third arm section neighboring the second arm section may have a 15 mm rod attached thereto, and so on. In this way, the length of the optical path through the fluid sample is switched according to the length of the rod positioned in the optical path.

Although the embodiments described thus far have pertained to a switching mechanism 46 implemented as a rotational mechanism 48 actuated to rotate by a motor 26, other embodiments are possible, in which the rotational mechanism 48 is actuated to rotate, at least in part, by non-motorized forces. In such embodiments, the rotational mechanism 48 may be actuated to rotate by the flow of the fluid sample through the hollow chamber 34 of the flow cell 30. For example, the rotational mechanism 48 may be designed as a turbine-like mechanism in which the arm sections 50 include contoured surfaces to accommodate flow induced rotation, or in which contoured blades, in addition to the arm sections 50, are connected to the base plate 49 to accommodate flow induced rotation. A motor, such as the motor 26, may still be utilized to stabilize the rotational speed of the rotational mechanism 48, and to support synchronization with the light detector 14.

The fluid sample measurement state corresponds to the situation in which none of the rods 52 are positioned in the optical path 56 (i.e., not aligned with the windows 40a and 40b). In this situation, only the fluid sample is positioned in the optical path 56, whereby the light beam from the light source 12 passes through the fluid sample when passing through the flow cell 30, resulting in the light beam traversing the fluid sample through a first optical path length.

The reference measurement state corresponds to when one of the rods 52 is positioned in the optical path 56 (i.e., aligned with the windows 40a and 40b), resulting in both some fluid sample and the rod 52, being positioned in the optical path 56. In this situation, both the fluid sample and a portion of the rod 52 are positioned in the optical path 56 and are traversed by the light beam from the light source 12 when the light beam passes through the flow cell 30, resulting in the light beam traversing the fluid sample through a second optical path length that is shorter than the first path length. This is due to the fact that the light beam is narrower than the cross section of the rod 52, and therefore the light beam passes through a small amount of the fluid sample in the flow cell 30 before passing in its entirety through the rod 52 and then again through a small amount of the fluid sample before exiting the flow cell 30.

By analogy, the positioning of one of the rods 52 in the optical path 56 displaces some of the fluid sample out of the optical path 56, thereby reducing the amount of the fluid sample in the optical path 56 in the reference measurement state relative to the amount of the fluid sample in the optical path 56 in the fluid sample measurement state. As such, the reference measurement state and the fluid sample measurement state correspond to different thicknesses of the fluid sample in the optical path 56.

A first light intensity measurement is conducted when the flow cell 30 is in the fluid sample measurement state, and a second light intensity measurement is conducted when the flow cell 30 is in the reference measurement state. Based on the two measurements conducted for the different optical path lengths, the transmittance and concentration of the solute of the fluid sample is calculated by the processing unit 16.

Figure 12A:
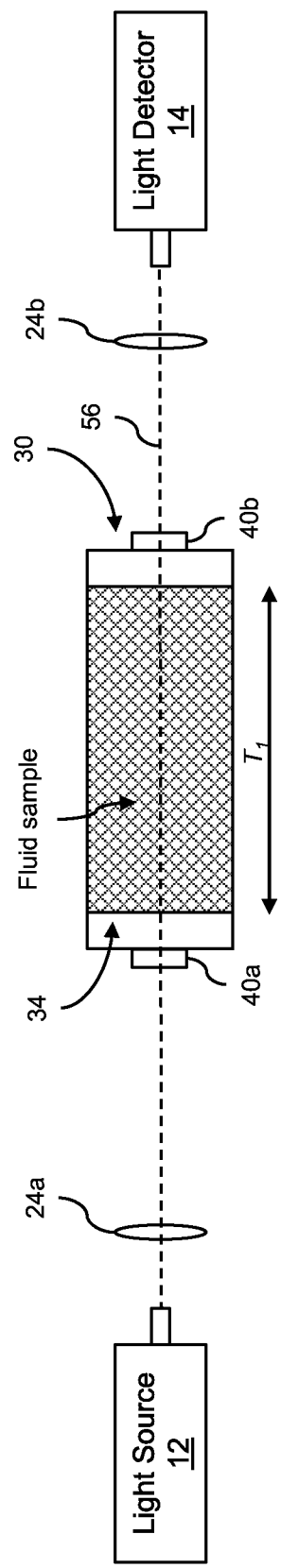
FIGS. 12A and 12B are schematic representations of the flow cell of FIG. 2, shown in a fluid sample measurement state and a reference measurement state, respectively, according to an embodiment of the invention.
Figure 12B:
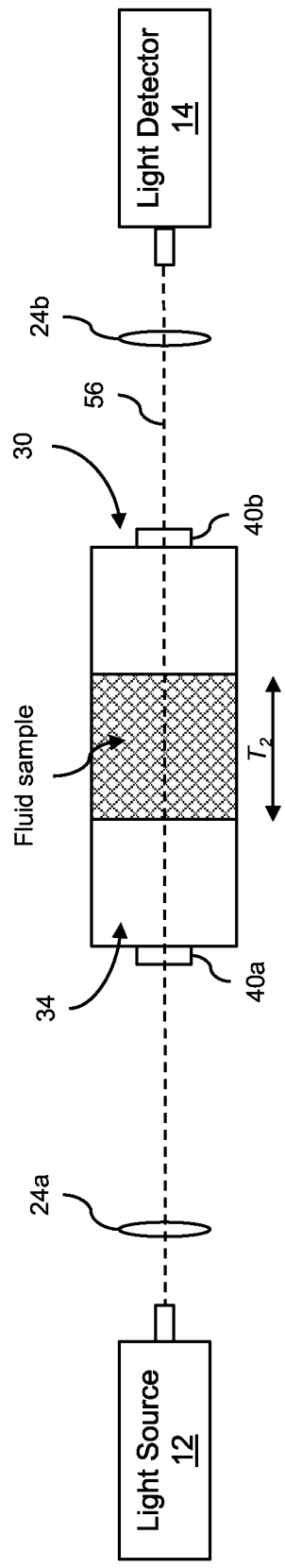

With continued reference to FIGS. 2-10, refer now to FIGS. 12A and 12B, schematic representations of the flow cell 30 when switched between the two measurement states, and the resultant change in the length of the optical path traversed by the light passing through the flow cell 30 in the two measurement states. The fluid sample in FIGS. 12A and 12B is represented by cross-hatched areas.

FIG. 12A corresponds to the fluid sample measurement state, in which the switching mechanism 46 is switched such that none of the rods 52 are positioned in the optical path 56, resulting in a thickness $T_1$ of the fluid sample in the optical path 56.

The thickness $T_1$ of the fluid sample in the optical path 56 in the fluid sample measurement state can be analogously understood as approximately the distance between the windows 40a and 40b.

FIG. 12B corresponds to the reference measurement state, in which the switching mechanism 46 is switched to position one of the rods 52 in the optical path 56, resulting in a thickness $T_2$ of the fluid sample in the optical path 56 (less than the thickness $T_1$).

The following paragraphs describe the calculations, performed by the algorithms executed by the processing unit 16, of the transmittance and concentration of the fluid sample based on signals produced by the light detector 14 in the two measurement states. $S_1$ and $S_2$ are the signal outputs of the light intensity measured by the light detector 14 when the flow cell 30 is in the fluid sample measurement state and the reference measurement state, respectively. $S_1$ can be expressed as follows:

$$S_1 = k_1 I_0 e^{-\alpha c T_1} \quad (5)$$

where $I_0$ is the intensity of the light radiation entering the optical system. Furthermore, $S_2$ can be expressed as follows:

$$S_2 = k_2 I_0 e^{-\alpha c T_2} \quad (6)$$

In equations (5) and (6), $k_1$ and $k_2$ are proportionality constants that account for the throughput of the optical system and the response of the light detector 14 in the respective switching states. Contrary to the example described with reference to equations (2)-(4), the difference between the constants $\tau_1$ and $\tau_2$ (which multiply the right sides of equations (5) and (6), respectively) can be reduced appreciably for three main reasons. Firstly, the geometric optical path traversed by the light beam in the two states is generally the same, with negligible differences attributed to the presence of the transparent rod in the reference state. The relatively constant geometry of the optical path is due to the same optics of the optical assembly 22 being used in both measurement states. Secondly, the rods 52 can be manufactured with one or more layers of anti-reflective material coated on the faces of the rods 52 that are traversed by the light beam (i.e., normal to the central axis 54), rendering the rods 52 almost ineffective in reducing their optical throughput. Thirdly, time changes of throughput due to degradation of the optical elements have the same effect in both measurement states.

Using equations (5) and (6), and assuming for simplicity that the difference between $k_1$ and $k_2$ is negligible, the variable c can be solved for, namely by taking the natural logarithm of the ratio of $S_1/S_2$. Accordingly, the concentration c can be expressed as follows:

$$c = \frac{\ln(S_2) - \ln(S_1)}{\alpha(T_1 - T_2)} \quad (7)$$

Note that in reference measurement state the reference material (i.e., rod 52) may be positioned in the optical path 56 such that substantially all of the fluid sample that was in the optical path 56 in the fluid sample measurement state is displaced by the rod 52, leaving substantially no fluid in the optical path 56 (i.e., $T_2 \approx 0$). Alternatively, the reference material (i.e., rod 52) may be positioned in the optical path 56 leaving a residual amount of fluid between the ends of the rod 52 and the nearest corresponding transparent surface of the flow cell 30. Any such residual amounts of fluid will have a corresponding optical throughput, which will equally multiply the signal equations above, and will therefore cancel out in the signal ratio calculation.

Although the embodiments described thus far have pertained to a switching mechanism implemented as a rotational mechanism actuated to rotate by a motor or induced by the flow of the fluid sample through the hollow chamber 34 of the flow cell 30, other embodiments are possible, in which the switching mechanism is implemented as various other mechanism. The following sections describe several embodiments directed to various implementations of the switching mechanism 46. It is noted that for clarity and conciseness, the lenses 24*a* and 24*b* are not shown in the drawings illustrating the embodiments directed to the various implementations of the switching mechanism 46. However, it should be understood by those of ordinary skill in the art that the lenses 24*a* and 24*b* (or equivalent optical components) are present in such embodiments as well. It is further noted that according to certain embodiments, the lens 24*a* may be absent, for example, in embodiments in which the light source 12 is a source which produces a directional beam (e.g., a laser). Further note that in such embodiments the lens 24*b* may also be absent, or may be present in order to focus the light onto the light detector 14.

Refer now to FIGS. 13A and 13B, another embodiment of the switching mechanism 46. The switching mechanism 46 of FIGS. 13A and 13B includes a transparent rod 60 that is deployed in the hollow chamber 34 and which acts as the reference material. The rod 60 is relatively thick in one dimension and relatively thin in another dimension and is rotatable about an axis along a third dimension that is normal to the aforementioned thick and thin dimensions. Furthermore, the axis of rotation of the rod 60 is normal to the optical path 56 and is normal or parallel to the plane of the paper. The rod 60 is constructed from, for example, sapphire or quartz or other transparent and inert material. The rod 60 is generally shaped as a parallelepiped, such that in both switching states the faces of the rod 60 that are in the optical path are parallel to each other. In certain non-limiting implementations, the rod 60 is cuboid (i.e., rectangular cuboid) in shape. The rod 60 may be similar to the rod 52 illustrated in FIG. 11, where the length L is significantly larger than the circular base diameter D (i.e., L>>D). As a result, the switching mechanism 46 rotates the rod 60 such that in a first position, the length L extends from the transparent window 40*a* toward the transparent window 40*b*, and such that in a second position, the length L extends in a direction normal to the direction that the length L extends when in the first position.

Although not shown in the drawings, the rod 60 may be connected to a motor, similar to the motor 26 illustrated in FIGS. 9 and 10, via a drive shaft or connecting rod that induces rotation of the rod 60. The rotation of the rod 60 changes the length of the optical path traversed by the light beam through the fluid sample.

Referring first to FIG. 13A, the flow cell 30 is shown in the fluid sample measurement state, in which the switching mechanism 46 is switched to rotate the rod 60 such that the thinner dimension of the rod 60 is positioned between the windows 40*a* and 40*b*. Similar to as shown schematically in FIG. 12A, this results in a thickness $T_1$ of the fluid sample in the optical path 56

Referring now to FIG. 13B, the flow cell 30 is shown in the reference measurement state, in which the switching mechanism 46 is switched to rotate the rod 60 such that the thicker dimension of the rod 60 is positioned between the windows 40*a* and 40*b*, in other words, such that the length L extends between the transparent windows 40*a* and 40*b*. Similar to as shown schematically in FIG. 12B, this results in a thickness $T_2$ of the fluid sample in the optical path 56

Figure 14A:
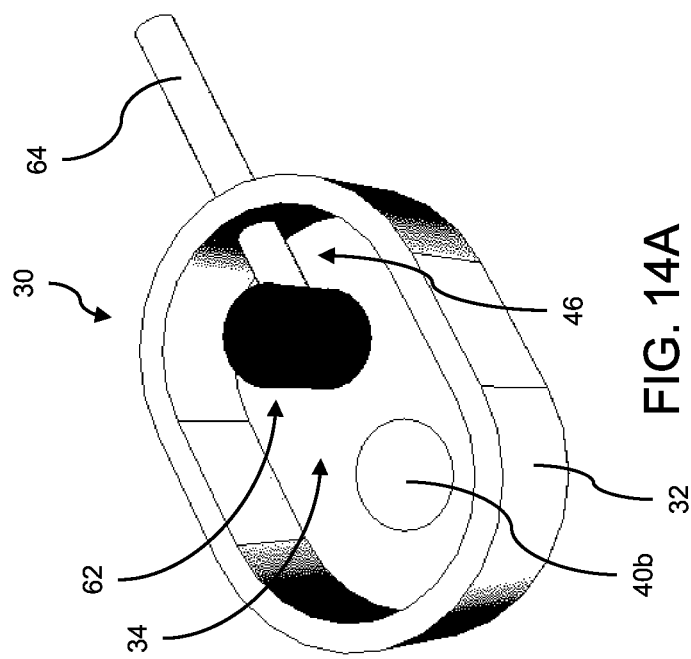
FIGS. 14A and 14B are schematic representations of a flow cell having a switching mechanism implemented as a sliding rod, shown in a fluid sample measurement state and a reference measurement state, respectively, according to an embodiment of the invention.
Figure 14B:
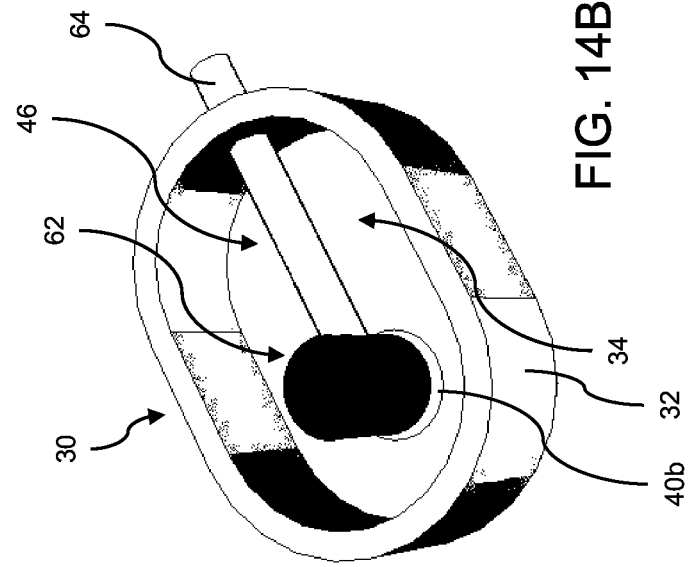

Refer now to FIGS. 14A and 14B, another embodiment of the switching mechanism 46. The switching mechanism 46 of FIGS. 14A and 14B is similar to that of the switching mechanism described with reference to FIGS. 13A and 13B, in that the switching mechanism includes a transparent rod 62, constructed from, for example, sapphire or quartz, that is deployed in the hollow chamber 34 and which acts as the reference material. The rod 62 may be cylindrical in shape or have a base surface of another shape that corresponds to the shape of the windows 40*a* and 40*b*. Unlike switching mechanism of the previous embodiment which uses rotational movement of the rod 60, the switching mechanism of the present embodiment is configured to switchably slide the rod 62 into and out of alignment with the windows 40*a* and 40*b*, thereby moving the rod 62 in and out of the optical path 56 by linear translational movement of the rod 62. The linear translational movement is induced by a drive shaft 64 that connects the rod 62 to a motor (not shown) which may be similar to the motor 26. The drive shaft 64 is operative to slide in and out of the hollow chamber 34 via, for example, an aperture formed in one of the sides of the flow cell body 32 sealed by a liquid seal to prevent leakage of the fluid sample out of the flow cell 30.

Note that FIGS. 14A and 14B illustrate a more schematic representation of the flow cell 30 than that illustrated in FIGS. 3-8. The flow cell illustrated in FIGS. 14A and 14B should be understood to possess the same general features of the flow cell illustrated in FIGS. 3-8, with the exception of the switching mechanism which is unique to the present embodiment. In addition, the flow cell of FIGS. 14A and 14B is shown with the cover removed to more clearly demonstrate the components of the switching mechanism of the present embodiment. As such, only the window 40*b* is shown in FIG. 14A and FIG. 14B.

Referring first to FIG. 14A, the flow cell 30 is shown in the fluid sample measurement state, in which the switching mechanism 46 is switched to position the rod 62 out of alignment with the windows 40*a* and 40*b*, and therefore out of the optical path. Similar to as shown schematically in FIG. 12A, this results in a thickness $T_1$ of the fluid sample in the optical path 56.

Referring now to FIG. 14B, the flow cell 30 is shown in the reference measurement state, in which the switching mechanism 46 is switched to position the rod 62 into alignment with the windows 40*a* and 40*b*, and therefore into the optical path Similar to as shown schematically in FIG. 12B, this results in a thickness $T_2$ of the fluid sample in the optical path.

Figure 15A:
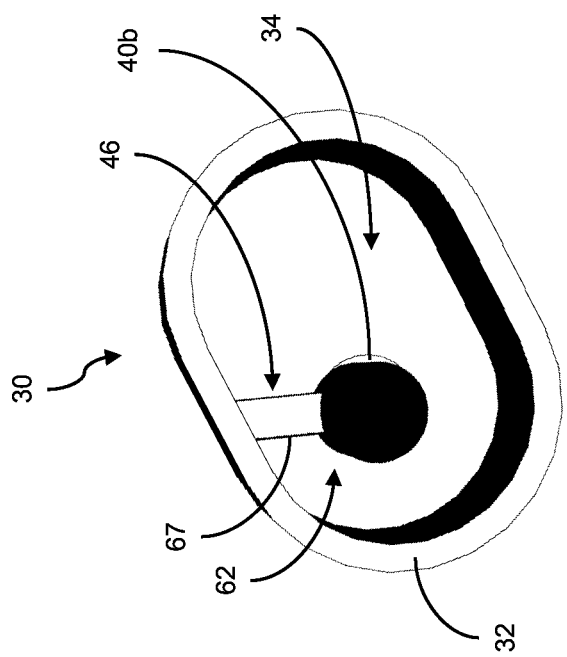
FIGS. 15A and 15B are schematic representations of a flow cell having a switching mechanism implemented as a rotatable arm, shown in a fluid sample measurement state and a reference measurement state, respectively, according to an embodiment of the invention.
Figure 15B:
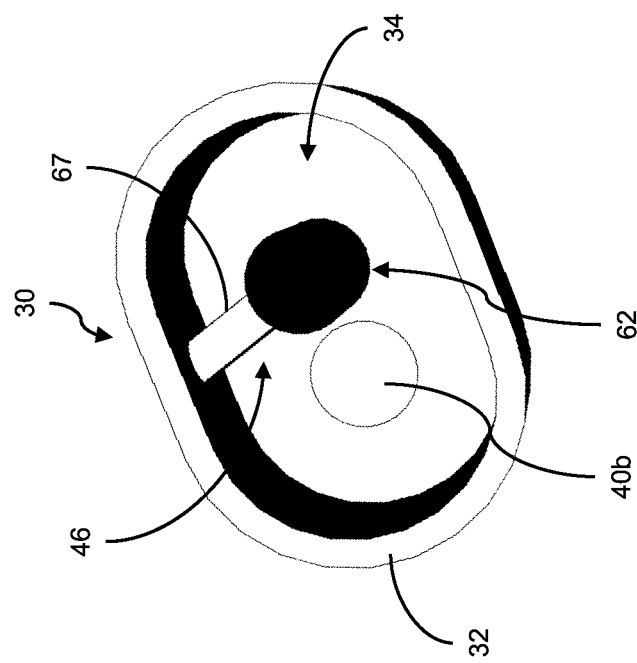

Note that the linearly movable drive shaft 64 of FIGS. 14A and 14B may be replaced by a rotatable arm 67 that partially rotates within the flow cell body 32 so as to induce movement of the rod 62, in and out of the optical path, as illustrated in FIGS. 15A and 15B.

Figure 16A:
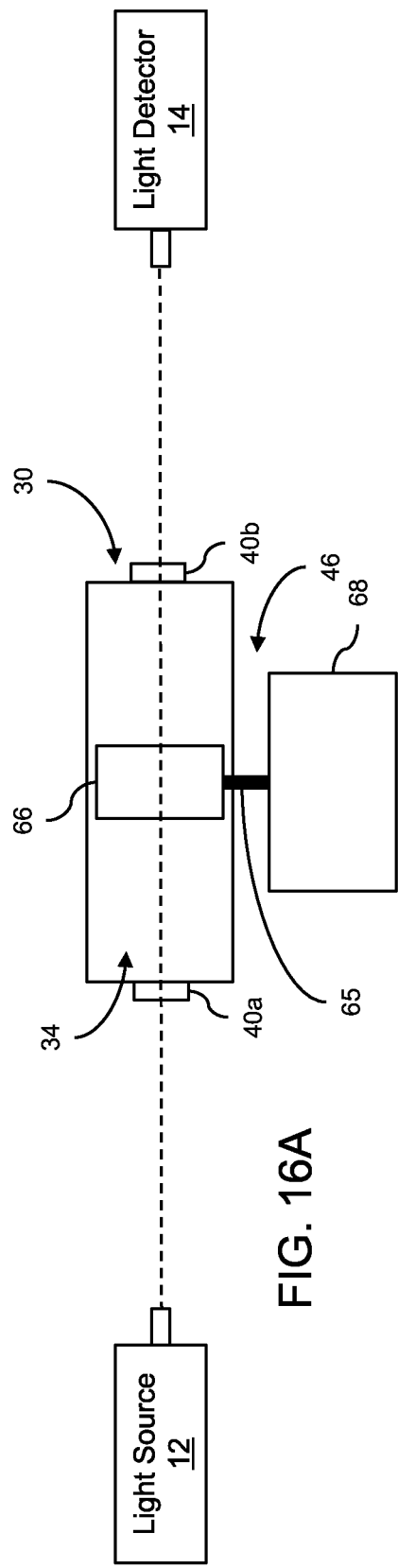
FIGS. 16A and 16B are schematic representations of a flow cell having a switching mechanism implemented as a dual sliding rod arrangement, shown in a fluid sample measurement state and a reference measurement state, respectively, according to an embodiment of the invention.
Figure 16B:
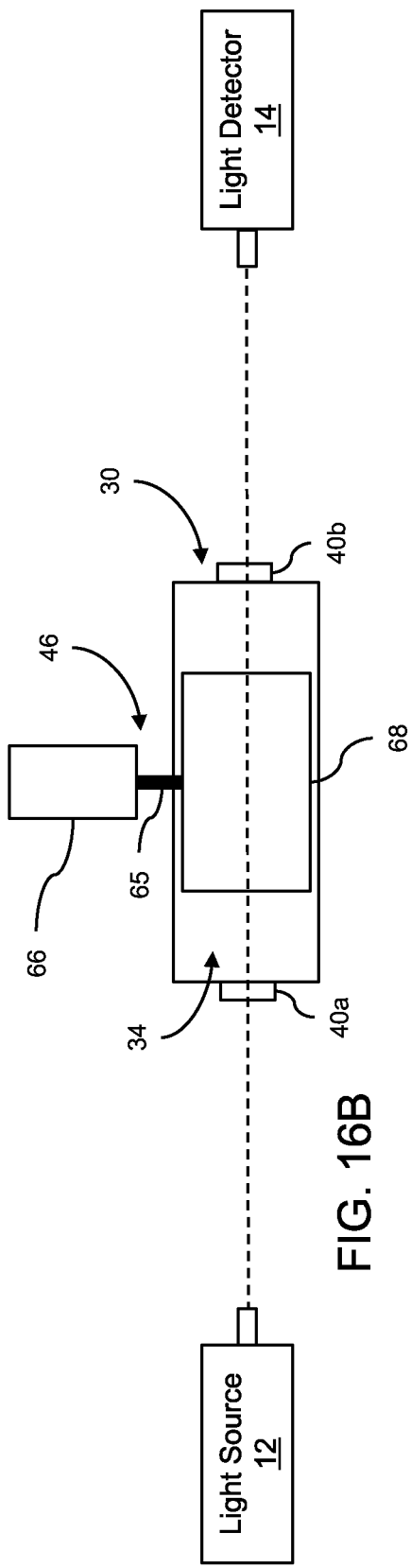

Refer now to FIGS. 16A and 16B, another embodiment of the switching mechanism 46. The switching mechanism 46 of FIGS. 16A and 16B is similar to that of the switching mechanism described with reference to FIGS. 14A and 14B. In particular, the switching mechanism 46 of FIGS. 16A and 16B utilizes a drive shaft 65 to effectuate linear translational movement of a reference material, similar to as in the embodiment of FIGS. 14A and 14B. However, the present embodiment utilizes a dual sliding rod arrangement that includes a first transparent rod 66 (of length $R_1$) and a second transparent rod 68 (of length $R_2 > R_1$), instead of a single transparent rod as described in the embodiment of FIGS. 14A and 14B. The rods 66 and 68 are jointly connected to the drive shaft 65, such that the rods 66 and 68 move in unison. The switching mechanism 46 laterally moves the drive shaft 65 to alternately position the rods 66 and 68 in and out of the optical path, thereby switching the length of the optical path between two different path lengths.

As in the previously described embodiments, the drive shaft 65 is connected to a motor (not shown) which may be similar to the motor 26.

Referring first to FIG. 16A, the flow cell 30 is shown in the fluid sample measurement state, in which the switching mechanism 46 is switched to position the first rod 66 into alignment with the windows 40a and 40b by laterally moving the drive shaft 65 in a first direction, and therefore into the optical path. Simultaneously, the second rod 68 is moved out of alignment with the 40a and 40b. Similar to as shown schematically in FIG. 12A, this results in a thickness $T_1$ of the fluid sample in the optical path.

Referring now to FIG. 16B, the flow cell 30 is shown in the reference measurement state, in which the switching mechanism 46 is switched to position the second rod 68 into alignment with the windows 40a and 40b by laterally moving the drive shaft 65 in a second direction opposite to the first direction, and therefore into the optical path. Simultaneously, the first rod 66 is moved out of alignment with the 40a and 40b Similar to as shown schematically in FIG. 12B, this results in a thickness $T_2$ of the fluid sample in the optical path, less than the thickness $T_1$.

Note that the constants $k_1$ and $k_2$ may be better equated when using the dual rod arrangement. This is due to the same amount of light loss being imparted from the fluid sample-rod interface in the two switching states.

It is noted that it may be particularly advantageous to use a transparent rod, or rods, as the reference material in embodiments in which the switching mechanism 46 is deployed inside the hollow chamber 34. The flow of the fluid sample through the hollow chamber 34, via the inlet port 42 and the outlet port 44, may act to flush and clean the end surfaces of the rod (i.e., the circular base portions) to remove any particles or materials which may build-up on the end surfaces over time.

It is noted that in all of the above described implementation of the switching mechanism 46, the relevant transparent rods (e.g., the rods 52, the rod 60, the rod 62, etc.) may be replaced by partially-transparent rods having known transmittance, or alternatively by chambers which contain the same solvent as the fluid sample without solute, a solution made of the same solvent and an accurately known concentration of the same solute material, or a fluid of known transmittance (e.g., air or deionized water). Such chambers have surfaces constructed from a material transparent in the spectrum of the light emitted by the light source 12.

Refer now to FIGS. 17A and 17B, another embodiment of the switching mechanism 46. The switching mechanism 46 of FIGS. 17A and 17B includes a piston arrangement 70 that includes a fixed transparent window 72 and a moveable transparent window 74. The transparent windows 72 and 74 are parallel to each other and are constructed from a material that is transparent in the spectrum of the light emitted by the light source 12, such as, for example, sapphire or quartz. The fixed transparent window 72 is positioned proximate to one of the front surface or the rear surface of the flow cell body 32 and is aligned with the transparent windows 40a and 40b. The moveable transparent window 74 is controllably moveable, in a linear fashion, towards and away from the fixed transparent window 72 and is aligned with the transparent windows 40a and 40b. The controlled movement of the moveable transparent window 74 effectively adjusts the amount of the fluid sample in the optical path, effectively switching the length of the optical path between two different path lengths. The movement of the moveable transparent window 74 may be controlled by a motor (not shown) which may be similar to the motor 26.

Referring first to FIG. 17A, the flow cell 30 is shown in the fluid sample measurement state, in which the switching mechanism 46 is switched to position the moveable transparent window 74 away from the fixed transparent window 72 at a maximal distance $D_1$. Similar to as shown schematically in FIG. 12A, this results in a thickness $T_1$ of the fluid sample in the optical path.

Referring now to FIG. 17B, the flow cell 30 is shown in the reference measurement state, in which the switching mechanism 46 is switched to position the moveable transparent window 74 closer to the fixed transparent window 72 at a minimal distance $D_2$. Similar to as shown schematically in FIG. 12B, this results in a thickness $T_2$ of the fluid sample in the optical path.

Although the embodiments described thus far have pertained to a flow cell having a single hollow chamber that contains a fluid sample together with a reference material, in which a switching mechanism adjusts the amount of the reference material in the optical path or the amount of the fluid sample in the optical path, other embodiments are possible, in which the reference material and the fluid sample are deployed in separate chambers.

Refer now to FIGS. 18A and 18B, an embodiment of a flow cell 30 in which the flow cell body 32 is subdivided into two separate chambers, a first hollow chamber 34 and a second hollow chamber 35. The fluid sample flows through the first hollow chamber 34, via inlet and outlet ports, similar to as described above with reference to FIGS. 2-16B. The reference material, which may be implemented as the same solvent as the fluid sample without solute, a solution made of the same solvent and an accurately known concentration of the same solute material, or a fluid of known transmittance (e.g., air or deionized water), is contained in the second hollow chamber 35. The pair of transparent windows 40a and 40b are deployed on opposing surfaces of the first hollow chamber 34, similar to as described in previous embodiments. The second hollow chamber 35 includes a pair of transparent windows 41a and 41b deployed on opposing surfaces of the second hollow chamber 35. The switching mechanism 46 includes a drive shaft 80 that interconnects the hollow chambers 34 and 35, such that the hollow chambers 34 and 35 laterally move in unison. The switching mechanism 46 laterally moves the drive shaft 80 to alternately position the hollow chambers 34 and 35, and thereby the fluid sample and the reference material, in and out of the optical path. As in the previously described embodiments, the drive shaft 80 may be connected to a motor (not shown) which may be similar to the motor 26

Referring first to FIG. 18A, the flow cell 30 is shown in the fluid sample measurement state, in which the switching mechanism 46 is switched to position the first hollow chamber 34 in the optical path and simultaneously move the second hollow chamber 35 out of the optical path.

Referring now to FIG. 18B, the flow cell 30 is shown in the reference measurement state, in which the switching mechanism 46 is switched to position the second hollow chamber 35 in the optical path and simultaneously move the first hollow chamber 34 out of the optical path.

Although most of the embodiments described thus far have pertained to various switching mechanisms actuated, at least in part, by a motor, for example, a stepper motor, connected to a drive shaft, other embodiments are possible, in which alternative actuators and driving arrangements are used to actuate the disclosed switching mechanisms, such as, for example a pneumatic actuator (e.g., an air operated piston arrangement) or magnetic actuator or hydraulic actuator. Such actuators may also perform partial and/or non-continuous rotation or movement of the reference material in and out of the optical path.

Implementation of the system and/or device of embodiments of the invention can involve performing or completing selected tasks manually, automatically, or a combination thereof. Moreover, according to actual instrumentation and equipment of embodiments of the system and/or device of the invention, several selected tasks could be implemented by hardware, by software or by firmware or by a combination thereof using an operating system.

As used herein, the singular form, "a", "an" and "the" include plural references unless the context clearly dictates otherwise.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A flow cell for analyzing a fluid sample, comprising:
a flow cell body for containing a reference material that includes at least one transparent rod, the flow cell body including:
at least one hollow chamber for containing the fluid sample, and
opposing surfaces each having at least one transparent portion thereof, wherein an optical path for light to traverse through the flow cell body is defined in part by the transparent portions; and
a switching mechanism operative to adjust an amount of the reference material deployed in the optical path by translationally moving the at least one transparent rod in and out of the optical path to effect switching of the flow cell between a reference measurement state corresponding to a first light intensity measurement, and a fluid sample measurement state corresponding to a second light intensity measurement.

2. The flow cell of claim 1, wherein the reference material further includes a second transparent rod, and wherein the two transparent rods are of different lengths.

3. The flow cell of claim 2, wherein the two transparent rods are jointly moveable.

4. The flow cell of claim 1, wherein the reference material is moveable so as to displace an amount of the fluid sample in the optical path.

5. The flow cell of claim 1, wherein the switching mechanism includes a piston arrangement.

6. The flow cell of claim 1, wherein the hollow chamber includes an inlet port and an outlet port providing a flow path for the fluid to flow through the hollow chamber.

7. The flow cell of claim 6, wherein the flow of the fluid through the hollow chamber acts to remove particles from at least one surface of the at least one transparent rod.

8. The flow cell of claim 1, wherein the switching mechanism is actuated by a motor operating in synchrony with a light detector.

9. The flow cell of claim 1, wherein the reference measurement state corresponds to a first optical path length, and wherein the fluid sample measurement state corresponds to a second optical path length.

10. The flow cell of claim 9, wherein the first optical path length corresponds to a first amount of the fluid sample in the optical path, and wherein the second optical path length corresponds to a second amount of the fluid sample in the optical path.

11. The flow cell of claim 1, wherein the hollow chamber is fixedly positioned in the optical path.

12. The flow cell of claim 1, wherein the transparent portions are implemented as a pair of transparent windows deployed on opposing surfaces of the hollow chamber.

13. The flow cell of claim 1, wherein the at least one transparent rod is deployed in the hollow chamber together with the fluid sample.

14. The flow cell of claim 1, wherein the optical path is further defined in part by a static lens arrangement that includes a first lens and a second lens, and wherein the transparent portions are positionable between respective lenses of the static lens arrangement.

15. A system for analyzing a fluid sample, comprising:
a flow cell including:
a flow cell body for containing a reference material including at least one transparent rod, and
at least one hollow chamber for containing the fluid sample;
a static optical arrangement including at least a first and a second lens for directing light from a light source, through the flow cell body, to a light detector;
at least a first and a second transparent surface deployed on opposing surfaces of the flow cell body, the flow cell body positionable to align the first transparent with the first lens and the second transparent surface with the second lens, wherein an optical path through the flow cell body is defined in part by the transparent surfaces and the static optical arrangement; and
a switching mechanism operative to adjust an amount of the reference material deployed in the optical path by translationally moving the at least one transparent rod in and out of the optical path to effect switching of the flow cell between a reference measurement state corresponding to a first light intensity measurement, and a fluid sample measurement state corresponding to a second light intensity measurement.

16. The system of claim 15, further comprising: an optical fiber arrangement including a first optical fiber for guiding light into the flow cell to pass through the flow cell, and a second optical fiber for guiding the light that passed through the flow cell.

17. The system of claim 16, further comprising: a light source coupled to the first optical fiber.

18. The system of claim 16, further comprising: a light detector coupled to the second optical fiber for measuring an intensity of light passing through the flow cell body.

19. The system of claim 18, wherein the detector and the switching mechanism are configured to operate in synchrony.

20. The system of claim 18, further comprising: a processing unit including at least one processor coupled to the detector, the processing unit configured to: receive a first signal indicative of the intensity of light passing through the flow cell body when the flow cell is in the reference measurement state, receive a second signal indicative of the intensity of light passing through the flow cell body when the flow cell is in the fluid sample measurement state, and determine at least one of a concentration or a transmission of the fluid sample based in part on the received signals.

21. A flow cell for analyzing a fluid sample, comprising:
at least one hollow chamber for containing the fluid sample;
a pair of transparent windows deployed on opposing surfaces of the hollow chamber, each of the transparent windows aligned with a respective lens of a static lens arrangement to define a light path through the hollow chamber; and
a switching mechanism including at least one transparent rod deployed in the at least one hollow chamber and contacting the fluid sample, the switching mechanism operative to translationally move the at least one transparent rod in and out of light path so as to change the length of the light path through the hollow chamber between at least a first light path length and a second light path length.

22. A flow cell for analyzing a fluid sample, comprising:
a flow cell body for containing a reference material that includes at least one transparent rod, the flow cell body including:
at least one hollow chamber for containing the fluid sample, and
opposing surfaces each having at least one transparent portion thereof, wherein an optical path for light to traverse through the flow cell body is defined in part by the transparent portions; and
a switching mechanism including a rotational mechanism having at least one rotating arm having the at least one transparent rod attached thereto, the switching mechanism operative to adjust an amount of the reference material deployed in the optical path by rotating the rotational mechanism to alternately position the at least one transparent rod in and out of the optical path so as to effect switching of the flow cell between a reference measurement state corresponding to a first light intensity measurement, and a fluid sample measurement state corresponding to a second light intensity measurement.

23. The flow cell of claim 22, wherein the rotational mechanism includes a plurality of arms, and wherein each arm has a transparent rod coupled thereto.

24. The flow cell of claim 22, wherein the transparent rods of adjacent arms have different lengths.

25. The flow cell of claim 22, wherein the hollow chamber includes an inlet port and an outlet port providing a flow path for the fluid to flow through the hollow chamber, and wherein the switching mechanism is actuated by the flow of the fluid through the hollow chamber.

26. The flow cell of claim 22, wherein the hollow chamber includes an inlet port and an outlet port providing a flow path for the fluid to flow through the hollow chamber, and wherein the flow of the fluid through the hollow chamber acts to remove particles from at least one surface of the at least one transparent rod.

27. A system for analyzing a fluid sample, comprising:
a flow cell including:
a flow cell body for containing a reference material including at least one transparent rod, and
at least one hollow chamber for containing the fluid sample;
a static optical arrangement including at least a first and a second lens for directing light from a light source, through the flow cell body, to a light detector;
at least a first and a second transparent surface deployed on opposing surfaces of the flow cell body, the flow cell body positionable to align the first transparent with the first lens and the second transparent surface with the second lens, wherein an optical path through the flow cell body is defined in part by the transparent surfaces and the static optical arrangement; and
a switching mechanism including a rotational mechanism that includes at least one rotating arm having the at least one transparent rod attached thereto, the switching mechanism operative to adjust an amount of the reference material deployed in the optical path by rotating the rotational mechanism to alternately position the at least one transparent rod in and out of the optical path so as to effect switching of the flow cell between a reference measurement state corresponding to a first light intensity measurement, and a fluid sample measurement state corresponding to a second light intensity measurement.

28. A flow cell for analyzing a fluid sample, comprising:
at least one hollow chamber for containing the fluid sample;
a pair of transparent windows deployed on opposing surfaces of the hollow chamber, each of the transparent windows aligned with a respective lens of a static lens arrangement to define a light path through the hollow chamber; and
a switching mechanism including a rotational mechanism that includes at least one rotating arm having at least one transparent rod attached thereto, the at least one transparent rod deployed in the at least one hollow chamber and contacting the fluid sample, the switching mechanism operative to rotate the rotational mechanism to alternately position the at least one transparent rod in and out of the light path so as to change the length of the light path through the hollow chamber between at least a first light path length and a second light path length.

29. A flow cell for analyzing a fluid sample, comprising:
a flow cell body for containing a reference material that includes a transparent rod, the flow cell body including:
at least one hollow chamber for containing the fluid sample, and
opposing surfaces each having at least one transparent portion thereof, wherein an optical path for light to traverse through the flow cell body is defined in part by the transparent portions; and
a switching mechanism operative to adjust an amount of the reference material deployed in the optical path by rotating the transparent rod about an axis of rotation that is substantially normal to the optical path so as to effect switching of the flow cell between a reference measurement state corresponding to a first light intensity measurement, and a fluid sample measurement state corresponding to a second light intensity measurement.

30. The flow cell of claim 29, wherein the hollow chamber includes an inlet port and an outlet port providing a flow path for the fluid to flow through the hollow chamber, and wherein the flow of the fluid through the hollow chamber acts to remove particles from at least one surface of the at least one transparent rod.

31. A system for analyzing a fluid sample, comprising:
   a flow cell including:
      a flow cell body for containing a reference material including a transparent rod, and
      at least one hollow chamber for containing the fluid sample;
   a static optical arrangement including at least a first and a second lens for directing light from a light source, through the flow cell body, to a light detector;
   at least a first and a second transparent surface deployed on opposing surfaces of the flow cell body, the flow cell body positionable to align the first transparent with the first lens and the second transparent surface with the second lens, wherein an optical path through the flow cell body is defined in part by the transparent surfaces and the static optical arrangement; and
   a switching mechanism operative to adjust an amount of the reference material deployed in the optical path by rotating the transparent rod about an axis of rotation that is substantially normal to the optical path so as to effect switching of the flow cell between a reference measurement state corresponding to a first light intensity measurement, and a fluid sample measurement state corresponding to a second light intensity measurement.

32. A flow cell for analyzing a fluid sample, comprising:
   at least one hollow chamber for containing the fluid sample;
   a pair of transparent windows deployed on opposing surfaces of the hollow chamber, each of the transparent windows aligned with a respective lens of a static lens arrangement to define a light path through the hollow chamber; and
   a switching mechanism including a transparent rod deployed in the at least one hollow chamber and contacting the fluid sample, the switching mechanism operative to rotate the transparent rod about an axis of rotation that is substantially normal to the light path so as to change the length of the light path through the hollow chamber between at least a first light path length and a second light path length.

* * * * *